United States Patent
Kazerooni et al.

(10) Patent No.: US 12,029,674 B2
(45) Date of Patent: Jul. 9, 2024

(54) TRUNK SUPPORTING EXOSKELETON AND METHOD OF USE

(71) Applicants: suitX, Inc., Emeryville, CA (US); The Regents of the University of California, Oakland, CA (US)

(72) Inventors: Homayoon Kazerooni, Berkeley, CA (US); Wayne Tung, Berkeley, CA (US); Michael McKinley, Berkeley, CA (US); Yoon Jung Jeong, Berkeley, CA (US)

(73) Assignees: The Regents of the University of California, Oakland, CA (US); suitX, Inc., Emeryville, CA (US)

( * ) Notice: Subject to any disclaimer, the term of this patent is extended or adjusted under 35 U.S.C. 154(b) by 996 days.

(21) Appl. No.: 16/375,231

(22) Filed: Apr. 4, 2019

(65) Prior Publication Data

US 2019/0231574 A1 Aug. 1, 2019

Related U.S. Application Data

(63) Continuation of application No. 14/704,901, filed on May 5, 2015, now Pat. No. 10,357,392, which is a
(Continued)

(51) Int. Cl.
*A61F 5/02* (2006.01)
*A61F 5/01* (2006.01)
*A61H 3/00* (2006.01)

(52) U.S. Cl.
CPC .......... *A61F 5/02* (2013.01); *A61F 5/01* (2013.01); *A61H 3/00* (2013.01)

(58) Field of Classification Search
CPC ...... A61H 1/02; A61H 1/0237; A61H 1/0244; A61H 1/0292; A61H 3/00;
(Continued)

(56) References Cited

U.S. PATENT DOCUMENTS 903,403 A * 11/1908 Quick .................... A61F 5/028
602/20
1,008,500 A * 11/1911 Thornton ............... A61F 5/028
602/19
(Continued)

FOREIGN PATENT DOCUMENTS

CN 201934433 U 8/2011
CN 108471865 A 8/2018
(Continued)

OTHER PUBLICATIONS

English translation of KR-20130111763-A. (Year: 2013).*
(Continued)

*Primary Examiner* — Justine R Yu
*Assistant Examiner* — Christopher E Miller
(74) *Attorney, Agent, or Firm* — Sterne, Kessler, Goldstein & Fox P.L.L.C.

(57) ABSTRACT

An exoskeleton includes two torque generators, thigh links, and a supporting trunk rotatably coupled to the thigh links. When a wearer bends forward in the sagittal plane such that the supporting trunk extends beyond a predetermined angle A with respect to vertical, at least one of the torque generators imposes a resisting torque between the supporting trunk and a corresponding thigh link, thus imposing a force onto a wearer's trunk and thighs to aid in supporting the wearer in a bent position. The torque generators may be active or passive torque generators. When the supporting trunk does not extend beyond the predetermined angle A, the torque generators do not impose resisting torques between the supporting trunk and thigh links during the entire range of motion of the thigh links, thus enabling a wearer to walk, run, and sit without constraint while in a substantially upright position.

32 Claims, 28 Drawing Sheets

Related U.S. Application Data continuation of application No. 14/480,549, filed on Sep. 8, 2014, now Pat. No. 9,022,956, which is a continuation-in-part of application No. 14/125,117, filed as application No. PCT/US2012/041891 on Jun. 11, 2012, now Pat. No. 9,655,762.

(60) Provisional application No. 61/495,484, filed on Jun. 10, 2011.

(58) Field of Classification Search
CPC ...... A61H 2201/165; A61H 2201/1628; A61F 5/028; B25J 9/0006; B25J 9/1602
See application file for complete search history.

(56) References Cited

U.S. PATENT DOCUMENTS

| | | | |
|---|---|---|---|
| 1,191,769 A | | 7/1916 | Curts et al. |
| 1,202,851 A | | 10/1916 | Kelly |
| 1,409,326 A | | 3/1922 | Williamson |
| 2,778,358 A | * | 1/1957 | Keles ............... A61F 5/028 |
| | | | 602/19 |
| 2,906,260 A | | 9/1959 | Myers |
| 3,570,011 A | * | 3/1971 | Naig ............... A61F 5/02 |
| | | | 2/44 |
| 3,790,209 A | | 2/1974 | Littmann |
| 4,256,098 A | | 3/1981 | Swan et al. |
| 4,342,140 A | | 8/1982 | Lacey |
| 4,745,911 A | | 5/1988 | Bender |
| 4,829,989 A | * | 5/1989 | Deamer ........... A63B 21/00181 |
| | | | 602/19 |
| 5,127,897 A | | 7/1992 | Roller |
| 5,152,730 A | | 10/1992 | Hoffman |
| 5,176,622 A | | 1/1993 | Anderson et al. |
| 5,207,635 A | | 5/1993 | Richards et al. |
| 5,248,293 A | | 9/1993 | Hubbard et al. |
| 5,259,833 A | | 11/1993 | Barnett |
| 5,275,426 A | | 1/1994 | Tankersley |
| 5,314,404 A | | 5/1994 | Boughner et al. |
| 5,876,361 A | * | 3/1999 | Harris ............... A61F 5/024 |
| | | | 602/19 |
| 5,951,591 A | | 9/1999 | Roberts |
| 6,056,673 A | | 5/2000 | Arrecis |
| 6,283,348 B1 | | 9/2001 | Wang |
| 6,436,065 B1 | | 8/2002 | Mitchell |
| 7,553,266 B2 | | 6/2009 | Abdoli-Eramaki |
| 7,744,552 B1 | | 6/2010 | Babcock |
| 8,033,518 B2 | | 10/2011 | Schuchman |
| 8,060,945 B2 | | 11/2011 | Adarraga |
| 8,568,344 B2 | | 10/2013 | Ferguson et al. |
| 9,022,956 B2 | | 5/2015 | Kazerooni et al. |
| 9,655,762 B2 | | 5/2017 | Kazerooni et al. |
| 9,744,066 B2 | | 8/2017 | Kazerooni et al. |
| 10,285,843 B2 | | 5/2019 | Yangyuenthanasan et al. |
| 10,357,392 B2 | | 7/2019 | Kazerooni et al. |
| 2004/0232180 A1 | | 11/2004 | Badillo |
| 2005/0130815 A1 | | 6/2005 | Abdoli-Eramaki |
| 2005/0158117 A1 | | 7/2005 | Arnold et al. |
| 2007/0090143 A1 | | 4/2007 | Clayton, III et al. |
| 2008/0161738 A1 | | 7/2008 | Giesen |
| 2008/0228121 A1 | | 9/2008 | Hughes |
| 2009/0292369 A1 | | 11/2009 | Kazerooni et al. |
| 2010/0094185 A1 | | 4/2010 | Amundson et al. |
| 2010/0125230 A1 | | 5/2010 | Hurley |
| 2010/0298746 A1 | | 11/2010 | Shimizu et al. |
| 2011/0098617 A1 | | 4/2011 | Ferguson et al. |
| 2011/0105966 A1 | | 5/2011 | Kazerooni et al. |
| 2011/0111932 A1 | | 5/2011 | von Hoffmann et al. |
| 2011/0266323 A1 | | 11/2011 | Kazerooni et al. |
| 2012/0101415 A1 | * | 4/2012 | Goffer ............... A61H 3/00 |
| | | | 601/35 |
| 2012/0136292 A1 | | 5/2012 | Pepin |
| 2012/0172770 A1 | * | 7/2012 | Almesfer ............ A61H 1/0255 |
| | | | 601/23 |
| 2012/0184881 A1 | | 7/2012 | Kobayashi et al. |
| 2013/0131560 A1 | | 5/2013 | Ferguson et al. |
| 2013/0184626 A1 | * | 7/2013 | Kazerooni ............ A61F 5/02 |
| | | | 602/19 |
| 2014/0121573 A1 | | 5/2014 | Kazerooni et al. |
| 2014/0331457 A1 | | 11/2014 | Perreault |
| 2015/0142130 A1 | | 5/2015 | Goldfarb et al. |
| 2016/0206498 A1 | | 7/2016 | Kazerooni et al. |
| 2017/0196712 A1 | | 7/2017 | Kazerooni et al. |
| 2017/0360588 A1 | | 12/2017 | Yangyuenthanasan et al. |

FOREIGN PATENT DOCUMENTS

| | | |
|---|---|---|
| DE | 19652416 A1 | 6/1998 |
| DE | 19652516 A1 | 6/1998 |
| DE | 202009000076 U1 | 4/2010 |
| DE | 202009000076 U1 | 5/2010 |
| EP | 3376895 | 9/2018 |
| JP | 01274758 A | 11/1989 |
| JP | 03165765 A | 7/1991 |
| JP | H09552 A | 1/1997 |
| JP | 2007020672 A | 2/2007 |
| JP | 2007097636 A | 4/2007 |
| JP | 2007130234 A | 5/2007 |
| JP | 2007282991 A | 11/2007 |
| JP | 2009011818 A | 1/2009 |
| JP | 2015163180 A | 9/2015 |
| WO | 2010011848 A1 | 1/2010 |
| WO | 2012171000 A1 | 12/2012 |
| WO | 2017086946 A1 | 5/2017 |
| WO | 2019017949 A1 | 1/2019 |

OTHER PUBLICATIONS

English translation of Braune (DE 19652416). (Year: 1998).*
English translation of Keisinger (DE 202009000076). (Year: 2010).*
English translation of Kobayashi (WO 2011/036906). (Year: 2011).*
"U.S. Appl. No. 14/125,117, Examiner Interview dated Jan. 12, 2017", 4 pages.
"U.S. Appl. No. 14/125,117, Examiner Interview Summary dated Mar. 23, 2016", 4 pages.
"U.S. Appl. No. 14/125,117, Final Office Action dated Aug. 12, 2016", 19 pages.
"U.S. Appl. No. 14/125,117, Non Final Office Action dated Jan. 11, 2016", 20 pages.
"U.S. Appl. No. 14/125,117, Notice of Allowance dated Feb. 10, 2017", 8 pages.
"U.S. Appl. No. 14/704,901, Non Final Office Action dated Dec. 29, 2017", 26 pages.
"U.S. Appl. No. 14/704,901, Notice of Allowance dated Jan. 3, 2019", 9 pgs.
"U.S. Appl. No. 14/944,635, Examiner Interview Summary dated Mar. 21, 2017", 3 pages.
"U.S. Appl. No. 14/944,635, Examiner Interview Summary dated Apr. 27, 2017", 1 page.
"U.S. Appl. No. 14/944,635, Non Final Office Action dated Nov. 4, 2016", 24 pages.
"U.S. Appl. No. 14/944,635, Notice of Allowance dated Apr. 27, 2017", 11 pgs.
"U.S. Appl. No. 14/944,635, Restriction Requirement dated Jun. 27, 2016", 8 pages.
"U.S. Appl. No. 15/654,929, Examiner Interview Summary dated Dec. 19, 2018", 1 page.
"U.S. Appl. No. 15/654,929, Non Final Office Action dated May 15, 2018", 34 pages.
"U.S. Appl. No. 15/654,929, Non Final Office Action dated May 16, 2018", 27 pages.
"U.S. Appl. No. 15/654,929, Notice of Allowance dated Dec. 19, 2018", 12 pages.
"U.S. Appl. No. 15/654,929, Restriction Requirement dated Nov. 2, 2017", 6 pages.
"European Application Serial No. 15908939.0, Search Report dated Jun. 27, 2019", 15 pgs.

(56) References Cited

OTHER PUBLICATIONS

"International Application Serial No. PCT/US12/41891, Search Report and Written Opinion dated Sep. 24, 2012", 9 pgs.
"International Application Serial No. PCT/US15/61284, dated Apr. 11, 2016", 14 pages.
"Int'l Application Serial No. PCT/US15/61284, Int'l Preliminary Report on Patentability dated May 31, 2018", 11 pgs.
"Int'l Application Serial No. PCT/US15/61284, ISRWO dated Apr. 11, 2016", 26 pages.
"Int'l Application Serial No. PCT/US17/43057, Int'l Search Report and Written Opinion dated Nov. 2, 2017", 10 pages.
"Japanese Application Serial No. 2018-524811, Notice of Allowance dated Jul. 9, 2019", 12 pgs.
"Korean Application Serial No. 10-2013-7033493, Office Action dated Feb. 25, 2019", 29 pgs.

\* cited by examiner

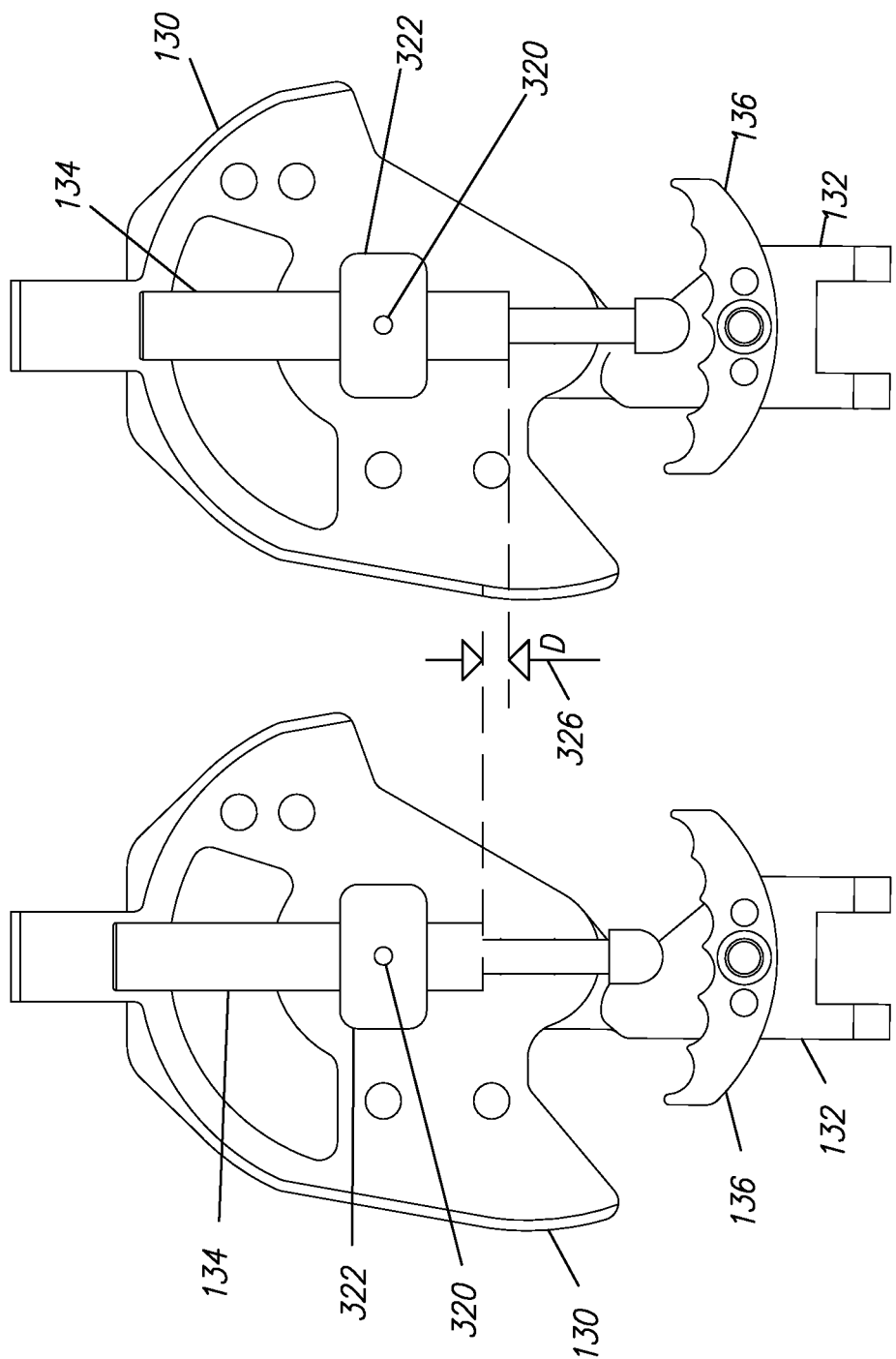

TRUNK SUPPORTING EXOSKELETON AND METHOD OF USE

CROSS-REFERENCE TO RELATED APPLICATIONS

This patent application is a continuation of U.S. patent application Ser. No. 14/704,901, filed May 5, 2015, which is a continuation of U.S. patent application Ser. No. 14/480, 549, filed Sep. 8, 2014, issued as U.S. Pat. No. 9,022,956 on May 5, 2015, which is a continuation-in-part of U.S. patent application Ser. No. 14/125,117, filed Dec. 11, 2013 and issued as U.S. Pat. No. 9,655,762 on May 23, 2017, which claims priority to PCT application PCT/US12/41891, filed Jun. 11, 2012, which claims the benefit of U.S. patent application 61/495,484, filed Jun. 10, 2011. All of these applications are incorporated herein by reference for all purposes along with all other references cited in this application.

GOVERNMENT LICENSE RIGHTS

This invention was made with government support under Grant No. 1317978 and Grant No. 1315427 awarded by the National Science Foundation (NFS). The government has certain rights in the invention.

BACKGROUND

The present disclosure pertains to the art of support devices for the human spine, more particularly to a trunk supporting exoskeleton configured to reduce the bending moment on a person's back during a forward bend.

In general, back support devices that are configured to assist a person in bending, lifting, or standing upright, or any combination of these, are known in the art. For example, see U.S. Pat. Nos. 6,436,065, 5,951,591, 5,176,622, and 7,744, 552. U.S. Pat. Nos. 1,409,326 and 4,829,989 describe devices where moment is created during a bend to counteract the moments from a person's trunk gravity weight. These systems utilize a passive, spring resistance to create a torque between the wearer's torso and legs. By creating a restorative moment at the hip, the probability of injury of the L5/S1 area of the spine is greatly reduced. Once the angle between torso and leg reaches a predetermined angle during stooping, squatting, or walking, the devices provide resistance; however, none of the devices differentiates between walking and bending or sitting and bending. This means the user cannot walk comfortably using these passive devices since the user's legs must push against the devices during walking. Similarly, the user cannot sit comfortably using these passive devices since the user's legs must push against the devices during sitting. This is uncomfortable and hazardous, preventing the user from moving around unrestricted, and is the most important reason to avoid the use of these systems in various industrial settings. Unlike the aforementioned devices, the technology described here differentiates between walking and bending and between sitting and bending. Even though the relative angle between the user's trunk and a swinging thigh is similar to each other in both cases of bending and walking (or bending and sitting), we have discovered a means by which they can be distinguished using minimal sensing and hardware.

SUMMARY

The present disclosure is directed to a trunk supporting exoskeleton configured to reduce the muscle forces in a wearer's back during forward lumbar flexion. In general, the exoskeleton includes first and second thigh links configured to couple to a wearer's thighs, and a supporting trunk configured to be coupled to a wearer's trunk. The supporting trunk is rotatably coupled to the thigh links to allow flexion and extension of the thigh links with respect to the supporting trunk. First and second opposing torque generators selectively create torque between the supporting trunk and respective thigh links.

In operation, when a wearer bends forward in the sagittal plane such that a predetermined portion of the supporting trunk deviates or extends beyond a predetermined angle with respect to vertical, at least one of the torque generators imposes a resisting torque between the supporting trunk and a corresponding thigh link. This causes the supporting trunk to impose a force onto a wearer's trunk, and the thigh links to impose forces onto the wearer's respective thighs, thereby helping to support the wearer while in the bent position. In a first embodiment, the exoskeleton includes a passive means for actuating the torque generators. More specifically, when a predetermined portion of the exoskeleton extends past the predetermined angle with respect to vertical, a resilient pendulum comes into contact with an engagement bracket, causing a resisting torque between the supporting trunk and a respective thigh link. In another embodiment, the exoskeleton includes an active means for actuating the torque generators, such as hydraulic motors, pneumatic motors, and electric motors.

The exoskeleton may include a signal processor including a controller, which produces a control signal to drive torque generators as a function of a set of input signals received by the signal processor. The input signals may be generated by one or more sensors incorporated into the exoskeleton, such as a velocity sensor, an accelerometer, a force sensor, or an angle sensor.

Importantly, when the supporting trunk does not extend beyond the predetermined angle with respect to vertical, the torque generators do not impose resisting torques between the supporting trunk and the thigh links during the entire range of wearer motion of the thigh links. Thus, a wearer is able to walk, run, and sit without any constraint while the wearer is in a substantially upright position.

In an implementation, a trunk supporting exoskeleton configured to be worn by a person to reduce the muscle forces in the wearer's back during forward lumbar flexion, the exoskeleton includes: a supporting trunk configured to contact a wearer's trunk; and two thigh links configured to couple to a wearer's thighs. The thigh links are rotatably coupled to the supporting trunk in a manner that allows for flexion and extension of thigh links relative to the supporting trunk along the human hip axes. There are two torque generators coupled to the supporting trunk and the thigh links. When the wearer bends forward in the sagittal plane, the torque generators impose a resisting torque between the supporting trunk and the thigh links, causing the supporting trunk to impose a force against a wearer's trunk and the thigh links to impose a force onto wearer's thighs.

In various implementations of the exoskeleton, at least one of the first and second torque generators includes: an upper bracket configured to be coupled to the supporting trunk; and a lower bracket configured to be coupled to one of the first and second thigh links and rotatably coupled to the upper bracket. A resilient pendulum is rotatably coupled to the upper bracket. An engagement bracket is coupled to the lower bracket. When a predetermined portion of the upper bracket extends beyond a predetermined angle from vertical, the resilient pendulum comes into contact with the engagement bracket, causing a resisting torque between the upper bracket and the lower bracket. When the predetermined portion of the upper bracket does not extend beyond a predetermined angle from vertical, the resilient pendulum is not in contact with the engagement bracket, and does not impose resisting torque between the upper bracket and the lower bracket.

The supporting trunk can include: a human interface configured to be coupled to a wearer's trunk; and a frame configured to be coupled to the human interface, where the frame is rotatably coupled to the first and second thigh links and allows for extension and flexion of the respective first and second thigh links relative to the supporting trunk. The human interface can include a back panel configured to interface with a wearer's back and a pair of shoulder straps configured to be coupled to the back panel. The human interface can include a back panel configured to interface with a wearer's back and a pair of shoulder straps configured to be coupled to the back panel and the frame.

The upper bracket can be manufactured as a part of the supporting trunk. The lower bracket can be manufactured as a part of the thigh link. The thigh link is adjustable for various lengths. The engagement bracket can be manufactured as a part of the lower bracket. The upper bracket can be manufactured as a part of the frame.

The frame can include a waist frame positioned behind the wearer approximately around the wearer's waist area where the first and second thigh links are rotatably coupled to the waist frame allowing for extension and flexion of the respective first and second thigh links relative to the waist frame. The frame can include a spine frame positioned behind the wearer and coupled to the waist frame. The frame can include a spine frame positioned behind the wearer and rotatably coupled to the waist frame allowing for side-to-side motion of the spine frame relative to the waist frame. The spine frame can be adjustable in its length. The frame is adjustable to accommodate wearers of various sizes.

The frame can include a waist frame substantially parallel with the person's hip line and a spine frame substantially parallel with the person's spine where the waist frame and the spine frame rotate relative to each other. The frame can include at least one resilient element that resists the rotation of the spine frame relative to the waist frame. The resilient element can include an element or combination of elements selected from a group consisting of gas spring, air spring, leaf spring, torsional spring, compression spring, linear spring and tensile spring.

The thigh link can further include a rotary joint allowing for rotation of the thigh link relative to the lower bracket. The resilient pendulum is rotatably coupled to the upper bracket where the rotating point location of the resilient pendulum relative to the upper bracket is adjustable. A holding block can be rotatably coupled to the upper bracket and the resilient pendulum is secured to the holding block. A mass can be coupled to the resilient pendulum and its location relative to the resilient pendulum can be adjusted to produce various natural oscillation frequencies.

The resilient element includes an element or combination of elements selected from a group consisting of gas spring, air spring, leaf spring, torsional spring, compression spring, linear spring and tensile spring. The torque generator can further include a locking system to prevent the rotational motion of the resilient pendulum relative to the upper bracket.

The locking system, among other things, can include a cover bracket coupled to the upper bracket and a moving bracket capable of moving relative to the cover bracket. When the moving bracket is in its unlocked position, it will not prevent the resilient pendulum from rotating relative to the upper bracket. When the moving bracket is in its locked position, the moving bracket prevents the resilient pendulum from rotating relative to the upper bracket.

The moving bracket, among other components, can include a protrusion where when the moving bracket is in its first position, the protrusion will not prevent the motion of resilient pendulum with respect to the moving bracket. When the moving bracket is in its second position, the protrusion will interfere the rotation of the resilient pendulum and prevent the motion of resilient pendulum with respect to the moving bracket.

In an implementation, a trunk supporting exoskeleton configured to be worn by a person to reduce the muscle forces in the wearer's back during forward lumbar flexion, the exoskeleton includes: a supporting trunk configured to support a wearer's chest; and first and second thigh links configured to couple to a wearer's thighs. Each of the first and second thigh links is rotatably coupled to the supporting trunk in a manner that allows for flexion and extension of respective first and second thigh links relative to the supporting trunk. An antimoving support is configured to couple the person and the trunk supporting exoskeleton in a manner such that it impedes the trunk supporting exoskeleton from moving upwardly toward the person's shoulder when the person is bending. There are first and second torque generators. Each of the first and second torque generators is configured to generate torque between the respective first and second thigh links and the supporting trunk. When a wearer bends forward in the sagittal plane such that a predetermined portion of the supporting trunk extends beyond a predetermined angle from vertical, at least one of the first or second torque generators imposes a resisting torque between the supporting trunk and at least one of the first and second thigh links. This causes the supporting trunk to impose a force against a wearer's trunk and at least one of the first and second thigh links to impose a force onto a wearer's thigh.

The antimoving support can be a belt configured to couple the person hip area and to couple the supporting trunk at locations close to the rotation points of thigh links relative to supporting trunk in a manner such that forward rotation of the supporting trunk from a vertical line does not cause substantial motion for the seat harness. The antimoving support can be a seat harness configured to contact the person's buttock area and to couple the supporting trunk at locations close to the rotation points of thigh links relative to supporting trunk in a manner such that forward rotation of the supporting trunk from a vertical line does not cause substantial motion for the seat harness.

The antimoving support can include at least a thigh loop coupled to the supporting trunk and configured to loop around the person's thigh. The antimoving support can include at least a thigh loop coupled to a thigh link and configured to loop around the person's thigh. The antimoving support can include at least a thigh loop coupled to a frame and configured to loop around the person's thigh.

In an implementation, a trunk supporting exoskeleton configured to be worn by a person to reduce the muscle forces in the wearer's back during forward lumbar flexion, the exoskeleton includes: a supporting trunk configured to support a wearer's trunk; and two thigh links configured to couple to a wearer's thighs. The thigh links are rotatably coupled to the supporting trunk in a manner that allows for flexion and extension of thigh links relative to the supporting trunk. A belt is configured to couple the person and the trunk supporting exoskeleton in a manner such that it impedes the trunk supporting exoskeleton from moving upwardly toward the person's shoulder when the person is bending. Two torque generators are coupled to the supporting trunk and the thigh links. When the wearer bends forward in the sagittal plane, the torque generators impose a resisting torque between the supporting trunk and the thigh links, causing the supporting trunk to impose a force against a wearer's trunk and the thigh links to impose a force onto wearer's thighs.

Other objects, features, and advantages of the present disclosure will become apparent upon consideration of the following detailed description and the accompanying drawings, in which like reference designations represent like features throughout the figures.

BRIEF DESCRIPTION OF THE DRAWINGS

FIGS. 16A-16B depict an embodiment of torque generator;

DETAILED DESCRIPTION

Figure 1:
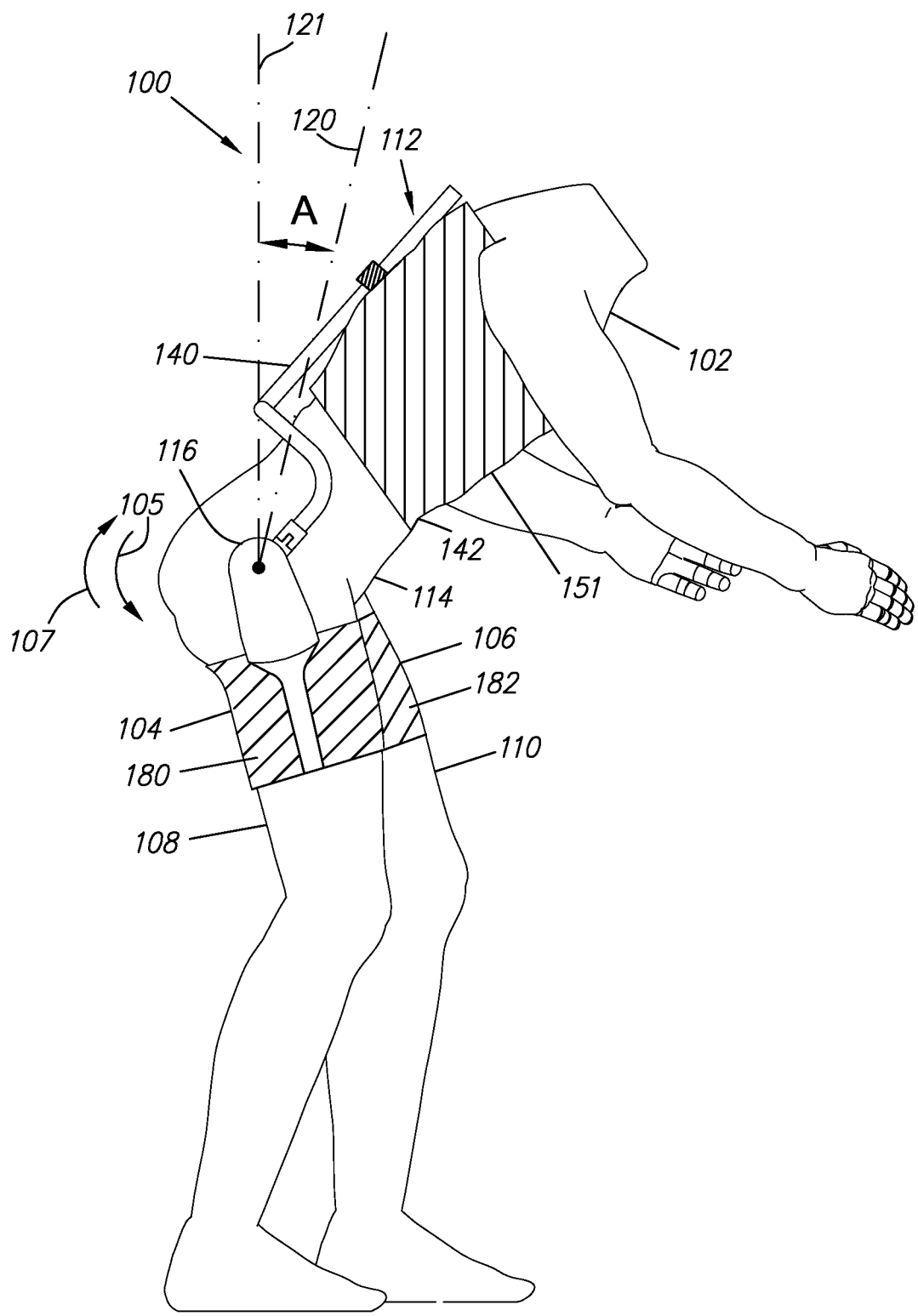
FIG. 1 shows a trunk supporting exoskeleton of the present disclosure on a forward leaning wearer.

FIG. 1 illustrates a trunk supporting exoskeleton 100 (referred to as exoskeleton 100) which is configured to be worn by a person or wearer. Exoskeleton 100, in addition to other functions, reduces the muscle forces in the wearer's back during forward lumbar flexion. In general, exoskeleton 100 comprises: two thigh links 104 and 106, which are configured to couple to a wearer's thighs 108 and 110; and a supporting trunk 112, which is configured to be coupled to the person's trunk 114. Supporting trunk 112 is rotatably coupled to thigh links 104 and 106, allowing for the flexion and extension along arrows 105 and 107 of thigh links 104 and 106 with respect to supporting trunk 112. Additionally, exoskeleton 100 includes first and second opposing torque generators 116 (only one of which is depicted in FIG. 1), capable of creating torques between supporting trunk 112 and respective first and second thigh links 104 and 106.

Figure 2:
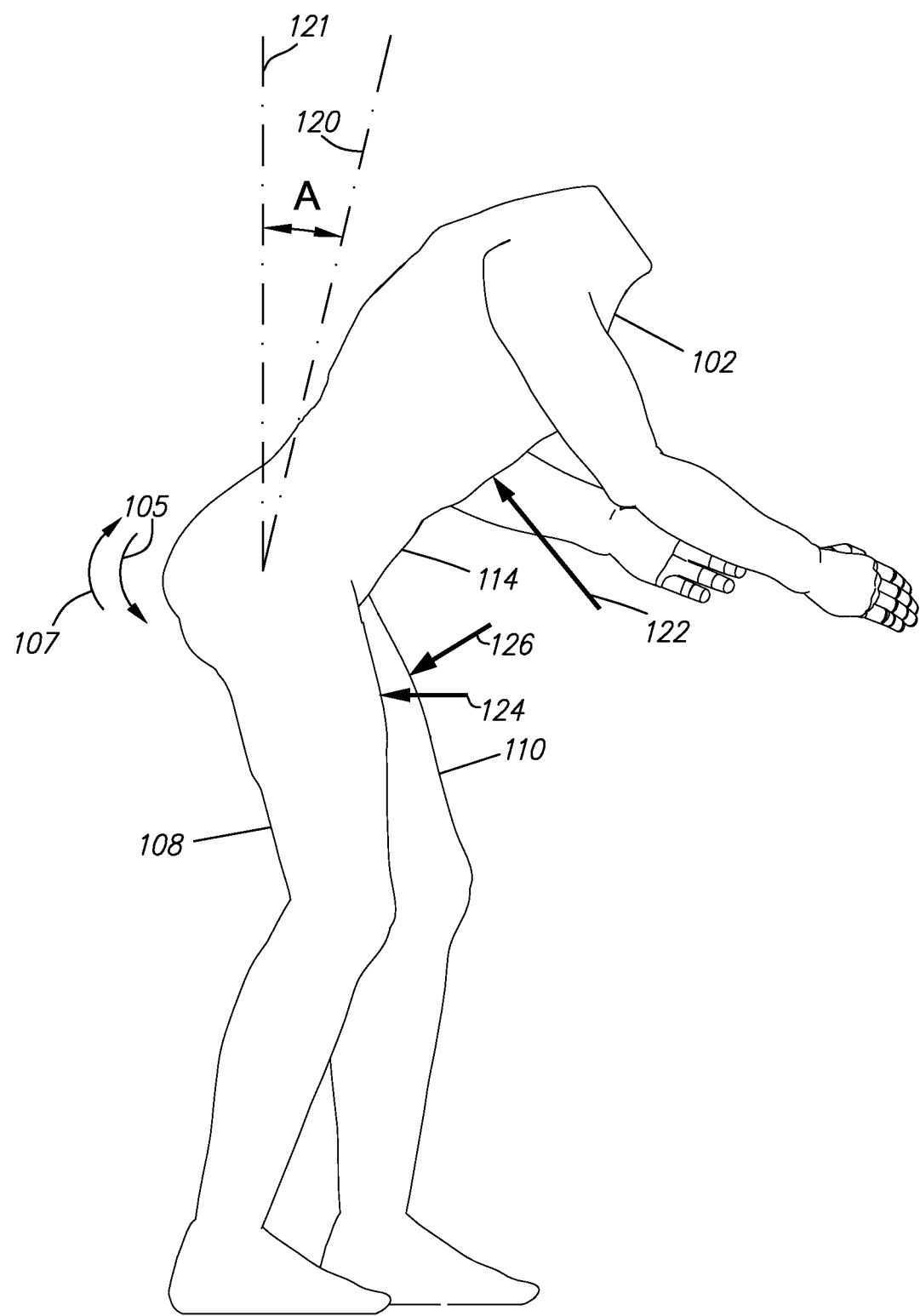
FIG. 2 depicts forces imparted on the wearer of FIG. 1, with the trunk supporting exoskeleton removed for clarity.

In operation, when a wearer bends forward in the sagittal plane such that supporting trunk 112 deviates beyond a straight line 120, at least one of torque generators 116 imposes a resisting torque between supporting trunk 112 and its corresponding thigh link 104 and 106. More specifically, line 120 extends at a predetermined angle from a straight vertical line 121, and represents a point beyond which torque generators are actuated. In other words, during forward lumbar flexion, when supporting trunk 112 extends beyond a predetermined angle from vertical, torque is imposed on thigh links 104 and 106. As shown in FIG. 2, this device causes supporting trunk 112 to impose a force 122 onto a person's trunk 114, and thigh links 104 and 106 to impose forces 124 and 126 onto the wearer's respective thighs 108 and 110. It should be understood that exoskeleton 100 could be configured such that torque is imposed on thigh links 104 and 106 when a predetermined portion of supporting trunk 112 extends beyond a predetermined angle from vertical. In some embodiments, torque may be imposed when any portion of supporting trunk 112 extends beyond line 120. In general, exoskeleton 100 can be configured such that torque is imposed on thigh links 104 and 106 when supporting trunk 112 shapes itself into a generally bent configuration.

Figure 3:
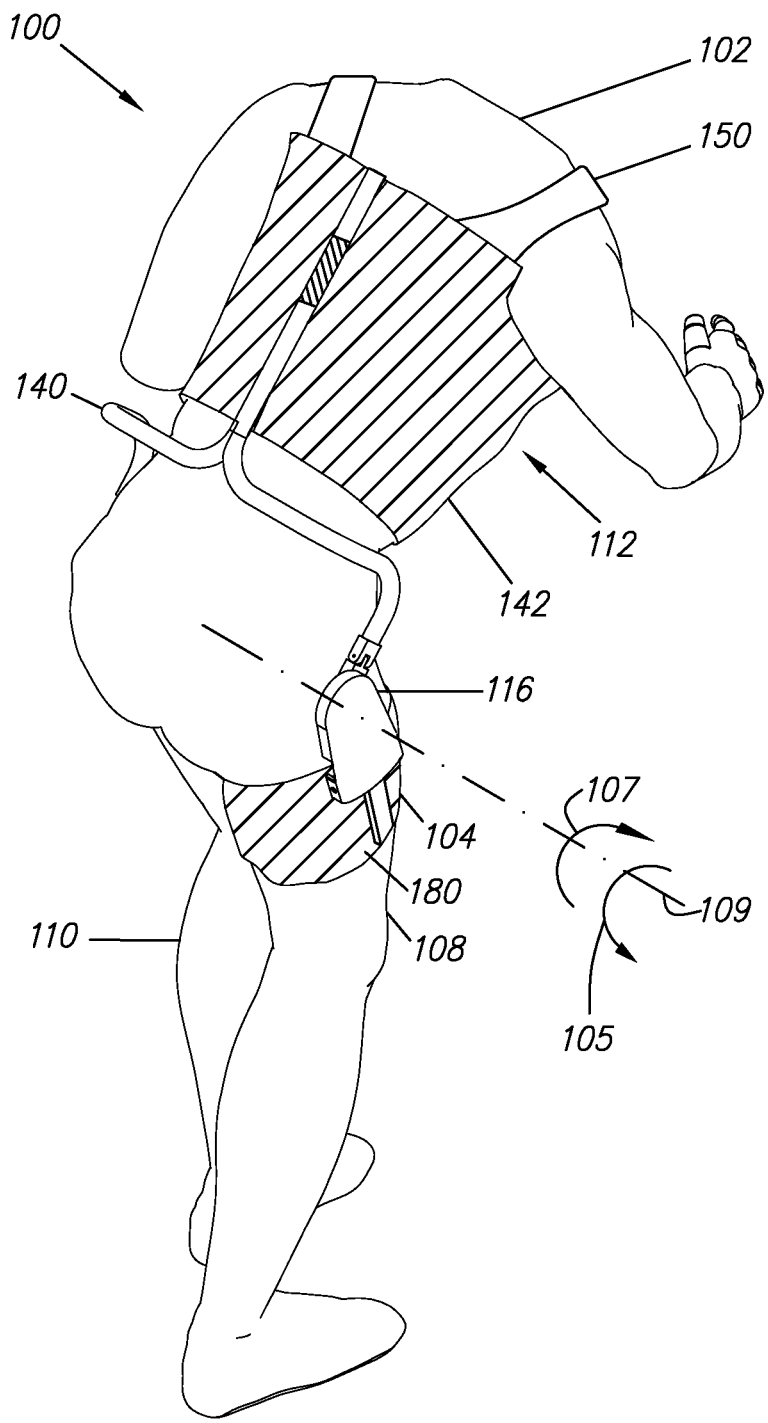
FIG. 3 depicts a back perspective view of a trunk supporting exoskeleton.

Further, in operation, when supporting trunk 112 is not deviated from line 120, torque generators 116 impose no resisting torques between supporting trunk 112 and thigh links 104 and 106 during the entire range of motion of thigh links 104 and 106. This is a unique characteristic of this device where the person can walk, run, and sit without any constraint as long as the person's trunk is substantially vertically aligned (i.e. not bent or not deviated beyond line 120). Torque generators 116 have unique characteristics where they only provide resisting torque when the human trunk is bent more than a predetermined value of an angle A, regardless of the human thighs' angles with respect to the person's trunk 114. As long as the person's trunk does not extend beyond line 120, regardless of the person legs positions and posture, no torque is generated by the torque generators 116. FIG. 3 is a perspective view where the flexion and extension of thigh link 104 with respect to supporting trunk 112 along axis 109 is depicted clearly.

Figure 4:
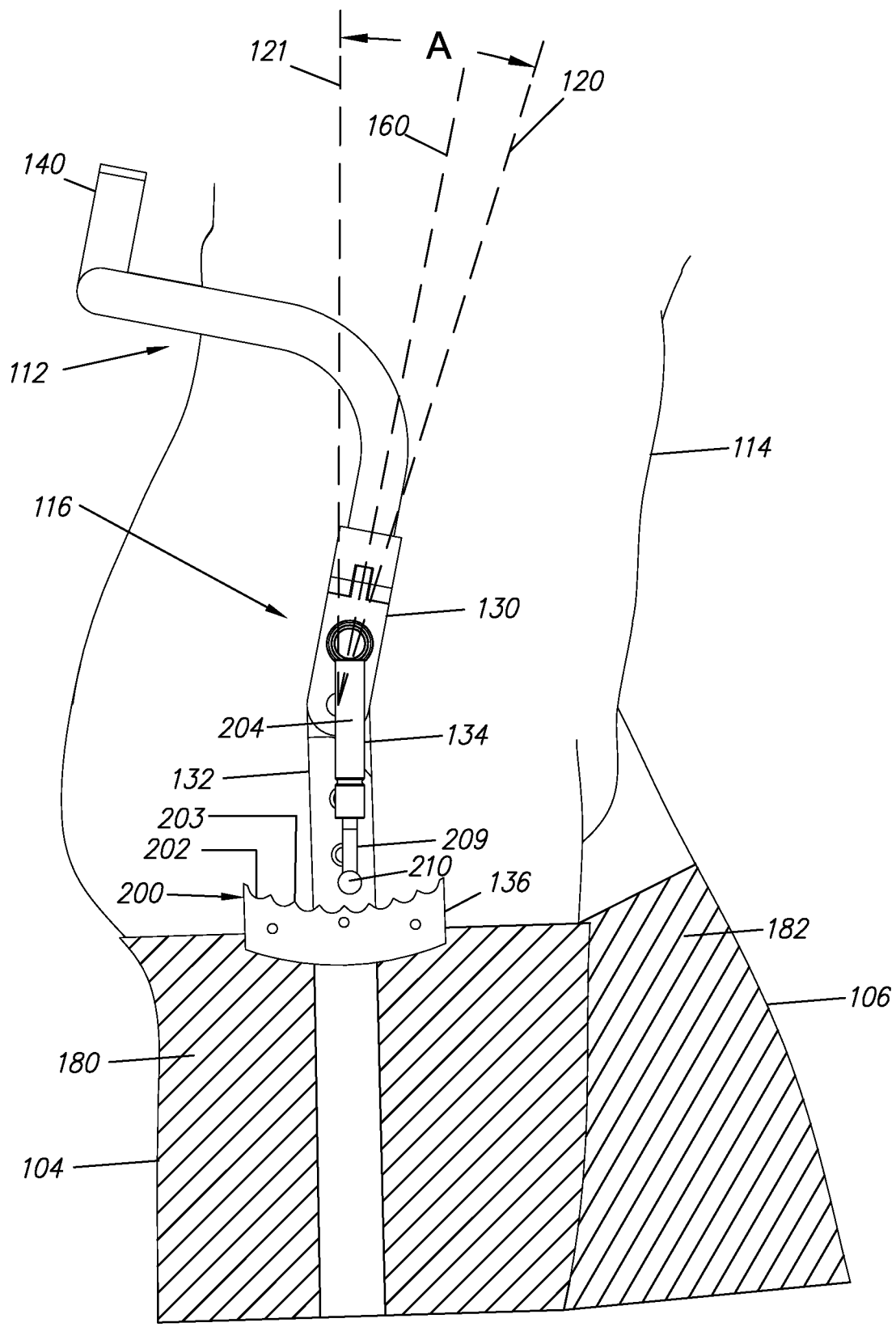
FIG. 4 is a side view of a passive torque generator embodiment of the present disclosure in an unengaged position
Figure 5:
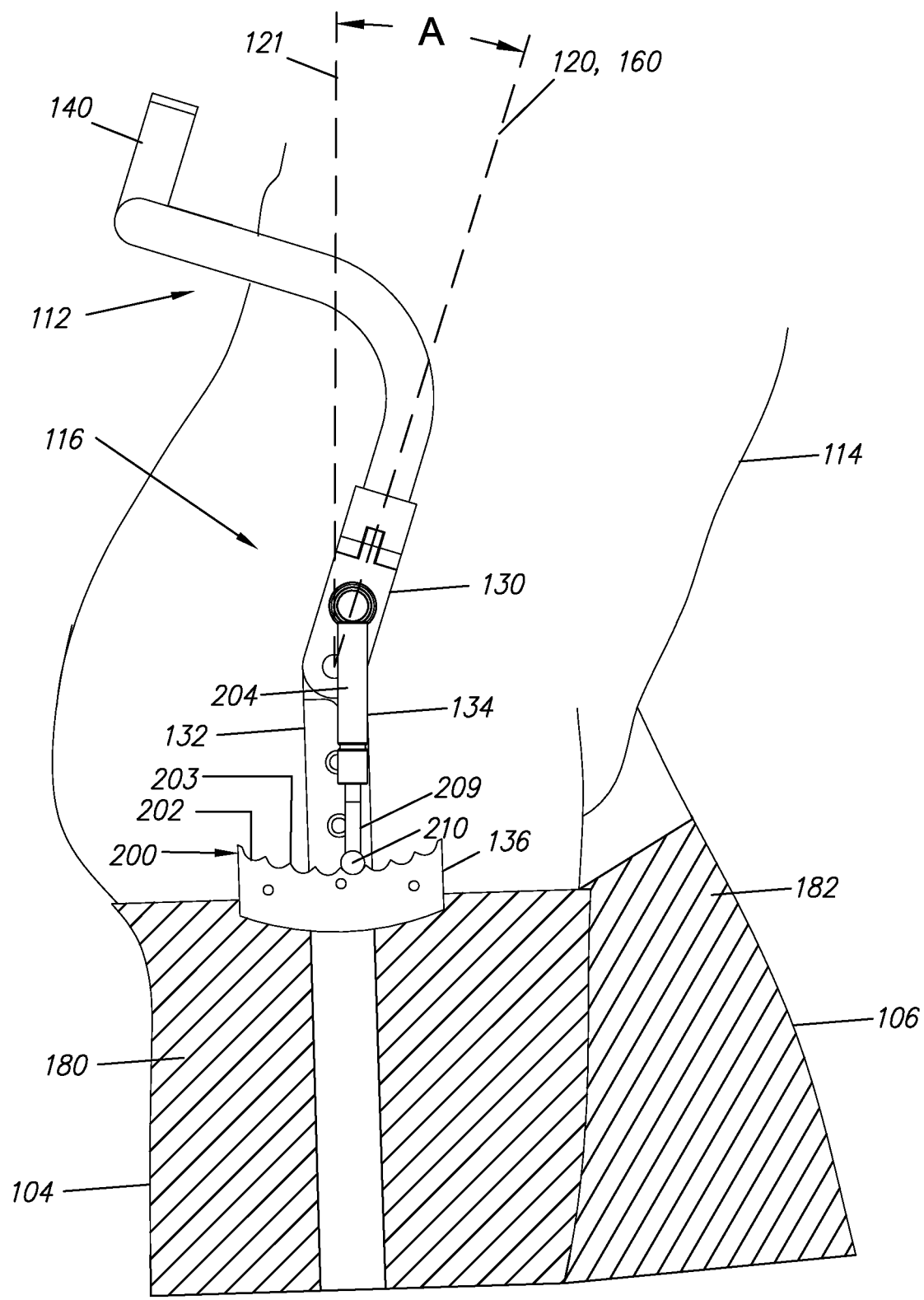
FIG. 5 is a side view of the passive torque generator of FIG. 4 in a first engaged position.

FIG. 4 describes an embodiment of torque generators 116 where respective covers have been removed. It should be noted that torque generators 116 are identical to each other and therefore, only the torque generator shown in FIG. 4 will be discussed in detail. As shown, torque generator 116 comprises: an upper bracket 130 coupled to supporting trunk 112; a lower bracket 132 coupled to thigh link 104 and rotatably coupled in a sagittal plane to upper bracket 130; a resilient pendulum 134 which is rotatably mounted on upper bracket 130; and an engagement bracket 136 which is securely coupled onto lower bracket 132. In operation, when a predetermined portion of upper bracket 130 extends past line 120, as depicted in FIG. 5, resilient pendulum 134 comes into contact with engagement bracket 136, causing a resisting torque between upper bracket 130 and lower bracket 132. When upper bracket 130 is not deviated from line 120, as depicted in FIG. 4, resilient pendulum 134 will not be in contact with engagement bracket 136, and no resisting torque is produced between upper bracket 130 and lower bracket 132. In some embodiments, resilient pendulum 134 behaves like a compression spring where deflections result in compression forces. In some embodiments, engagement bracket 136 and lower bracket 132 are a one-piece part.

Figure 6:
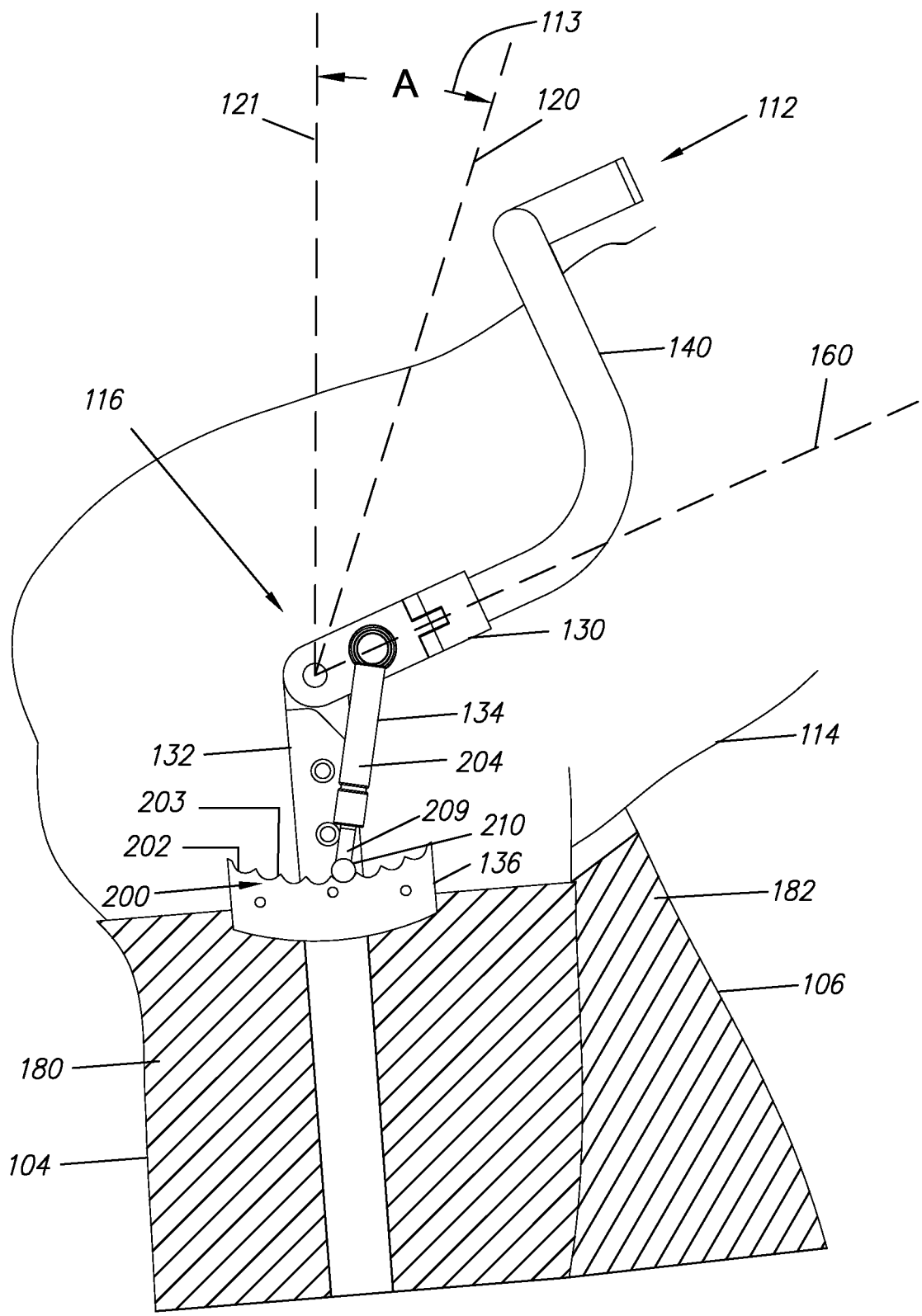
FIG. 6 is a side view of the passive torque generator of FIG. 4 in a second engaged position.

FIG. 6 shows a situation where a person has bent at the waist substantially and resilient pendulum 134 is compressed, such that the length is shortened substantially. In some embodiments as shown in FIG. 4, FIG. 5 and FIG. 6, resilient pendulum 134 comprises an air spring comprising cylinder 204 and piston 209 moving relative to each other. In some embodiments, resilient pendulum 134 is a coil spring. Engagement bracket 136 has a profile that does not allow the tip of resilient pendulum 134 to slide relative to engagement bracket 136. In the depicted embodiment, engagement bracket 136 has a profile that matches the circular profile of the tip of the resilient pendulum 134. More specifically, engagement bracket 136 includes a scalloped upper wall 200 including a plurality of curved divots 202 separated by peaks 203. Resilient pendulum 134 further includes a tip 210 in the form of a round knob sized to fit within each of curved divots 202. As depicted in FIG. 5, when a wearer bends beyond a predetermined point represented by line 120, tip 210 engages with one of curved divots 202 and is held in position by peaks 203, such that, upon further bending of the wearer, resilient pendulum 134 will be held in place and the resilient pendulum 134 will compress. In some embodiments, scalloped upper wall 200 or tip 210, or both, may include a frictional surface to prevent the sliding motion of tip 210 within a curved divot 202.

In some embodiments, torque generators 116 are active systems. Examples of active torque generators which can be utilized with the present disclosure include, without limitation, hydraulic motors, pneumatic motors, and electric motors, including, without limitation, alternating current (AC) motors, brush-type direct current (DC) motors, brushless DC motors, electronically commutated motors (ECMs), stepping motors, and combinations thereof. In some embodiments, torque generators 116 each include an electric motor and a transmission. The resistance supplied by first and second torque generators 116 between supporting trunk 112 and respective thigh links 104 and 106 impose a force onto the person's trunk 114 in the manner depicted in FIG. 1. These torques also cause thigh links 104 and 106 to impose forces onto the wearer's thighs 108 and 110.

Figure 10:
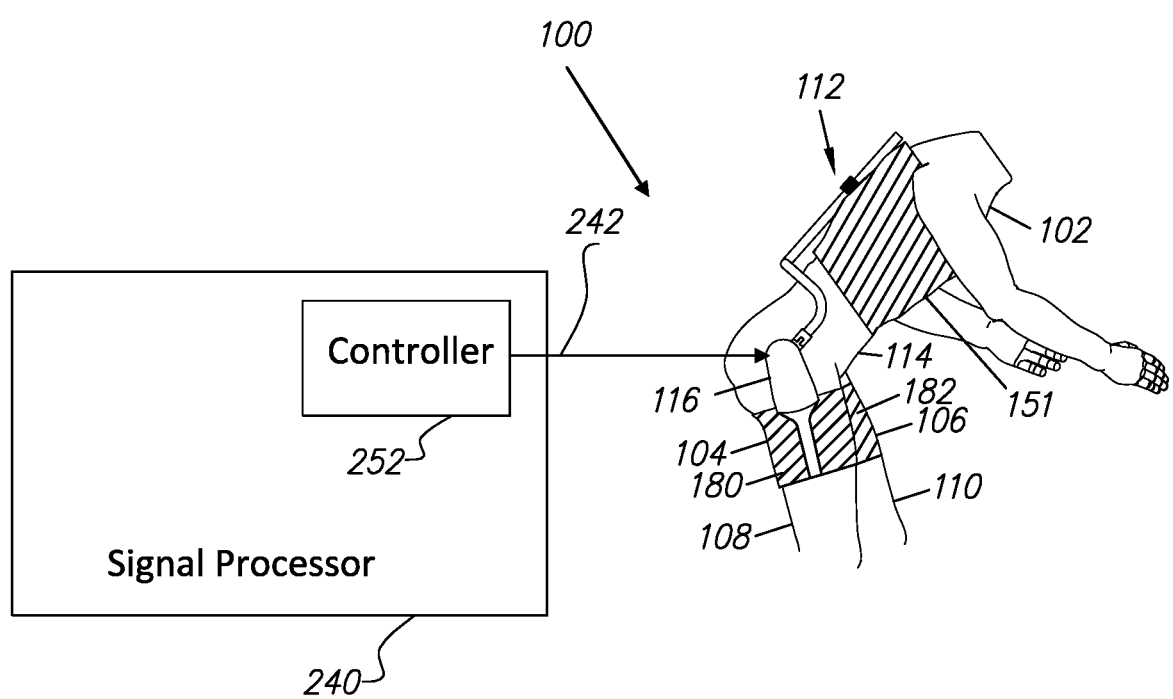
FIG. 10 depicts a signal processor of the present disclosure.
Figure 11:
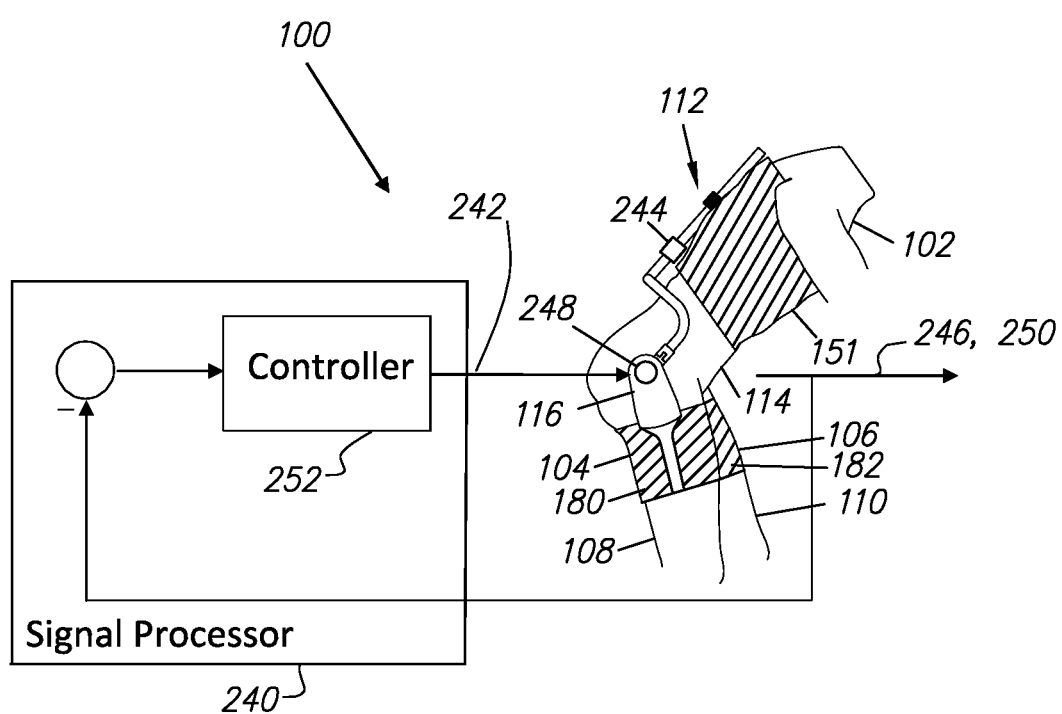
FIG. 11 depicts a first method of control of the present disclosure.

The manner in which the resistance torque can be automatically adjusted when an active torque generator is used will now be discussed with reference to FIGS. 10-12. In some embodiments, as shown in FIG. 10, exoskeleton 100 includes a signal processor 240 configured to produce a control signal 242 for torque generators 116, wherein control signal 242 drives torque generators 116. Signal processor 240 incorporates a controller 252 that produces control signal 242 for torque generators 116 as a function of a set of input signals that signal processor 240 receives. Examples of input signals that signal processor 240 receives include, without limitation, signals representing angles of thigh links 104 and 106 with respect to supporting trunk 112, signals representing the velocity of supporting trunk 112 with respect to thigh links 104 and 106, signals representing the acceleration of supporting trunk 112 with respect to thigh links 104 or 106, a signal representing the absolute angle of supporting trunk 112, a signal representing the absolute velocity of supporting trunk 112, a signal representing the absolute acceleration of supporting trunk 112, a signal representing at least one torque generator's movement, a signal representing at least one torque generator's speed, a signal representing at least one torque generator's acceleration, a signal representing at least one torque generator's torque, a signal representing at least one torque generator's force, a signal representing the person's movement, a signal representing the person's bending angle, a signal representing the person's bending velocity, a signal representing the person's bending acceleration, a signal representing the contact force between person 102 and supporting trunk 112, a signal representing an electromyography (EMG) signal from the person and combinations thereof.

Various sensors can be utilized to provide controller 252 with the necessary signal information. In one preferred embodiment depicted in FIG. 11, supporting trunk 112 includes a first sensor 244 generating a first signal 246 representing an output from first sensor 244. In a first example, first sensor 244 is an absolute angle sensor and first signal 246 is an absolute angle signal representing the angle that person 102 or supporting trunk 112 has bent forward relative to line 120 or vertical line 121 (shown in FIG. 1). However, it should be understood that first sensor 244 could be a velocity sensor, an accelerometer, or other type of movement sensor. Supporting trunk 112 can also include a second sensor 248 (shown in FIG. 11) generating a second signal 250 representing an output from second sensor 248. In one example, second sensor 248 is an angle sensor and second signal 250 is an angle signal representing the angle of supporting trunk 112 with respect to thigh links 104 or 106. In general, second sensor 248 is either included in the torque generators 116, installed on the same location on thigh links 104 or 106, or supporting trunk 112 that torque generator 116 are installed. However, it should also be understood that second sensor 248 could be a torque generator movement sensor, a torque generator speed sensor, a torque generator accelerometer, a torque generator torque or force sensor, or any type of standard movement sensor. In operation, as shown in FIG. 11, signal processor 240 produces control signal 242 for torque generators 116 as a function of first signal 246, or second signal 250, or both. That is, controller 252 utilizes first and second signals 246 and 250 as a feedback signal to generate control signal 242. The type of controller utilized dictates the magnitude of the resistance torque. One can find a variety of algorithms for controller 252 to perform the indicated task. In general, controllers with large gains lead to large resistance torques, while controllers with small gains result in smaller resistance torque.

Figure 12:
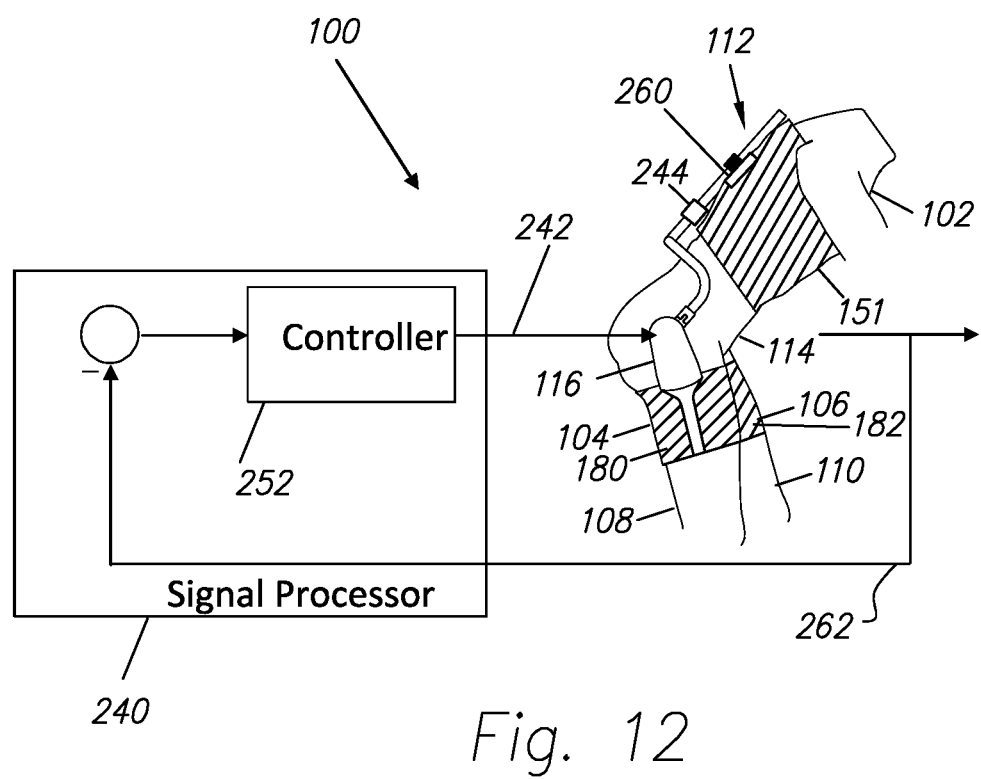
FIG. 12 depicts an alternative method of control of the present disclosure.

As shown in FIG. 12, exoskeleton 100 may also include a force or pressure sensor 260 generating a force or pressure signal 262 representing the force or pressure between person 102 and supporting trunk 112. In operation, signal processor 240 produces control signal 242 for torque generators 116 as a function of force or pressure signal 262. That is, controller 252 utilizes force or pressure signal 262 as a feedback signal to generate control signal 242.

From the discussion above, it should be understood that controller 252 could be programmed and configured to activate torque generators 116 in a variety of ways based on signals 246, 250, or 262, or any combination these, from sensors 244, 248, or 260, or any combination of these. In some embodiments, the resistance torque is a function of how much person 102 is bending forward. For example. In some embodiments, the resistance torque increases as person 102 bends forward. In some embodiments, the resistance torque is a function of the angle between person 102 and a line 120. In some embodiments, the resistance torque increases linearly as the angle between person 102 and vertical line 121 (shown in FIG. 2) increases. In some embodiments, the resistance torque is a function of how much supporting trunk 112 moves toward thigh links 104 or 106. In some embodiments, the resistance torque is a function of the angle between supporting trunk 112 and vertical line 121. In some embodiments, the resistance torque increases linearly as the angle between supporting trunk 112 and vertical line 121 increases. In some embodiments, the controller is configured to adjust the resistance torque imposed by the first and second torque generators to be generally constant for at least one segment of a bending movement of a wearer.

In some embodiments, as shown in FIG. 1 and FIG. 3, supporting trunk 112 comprises a human interface 142, which is configured to be coupled to a person's trunk 114, and a frame 140, which is configured to be coupled to human interface 142. Frame 140 is rotatably coupled to thigh links 104 and 106 allowing for extension and flexion of thigh links 104 and 106 relative to frame 140. Frame 140 comprises any material or combination of materials capable of performing the indicated functions. Examples of materials of frame 140 include, without limitation, aluminum materials, plastic materials, carbon fiber materials, metallic materials, and combinations thereof. In some embodiments, frame 140 comprises of plurality of components coupled or hinged to each other. From the discussion above, it should be understood that controller 252 could be programmed and configured to activate torque generators 116 in a variety of ways based on signals 246, 250, or 262, or any combination of these from sensors 244, 248, or 260, or any combination of these. In some embodiments, the resistance torque is a function of how much person 102 is bending forward. In some embodiments, the resistance torque increases as person 102 bends forward. In some embodiments, the resistance torque is a function of the angle between person 102 and a line 120. In some embodiments, the resistance torque increases linearly as the angle between person 102 and vertical line 121 (shown in FIG. 2) increases. In some embodiments, the resistance torque is a function of how much supporting trunk 112 moves toward thigh links 104 or 106. In some embodiments, the resistance torque is a function of the angle between supporting trunk 112 and vertical line 121. In some embodiments, the resistance torque increases linearly as the angle between supporting trunk 112 and vertical line 121 increases. In some embodiments, the controller is configured to adjust the resistance torque imposed by the first and second torque generators to be generally constant for at least one segment of a bending movement of a wearer.

Figure 7:
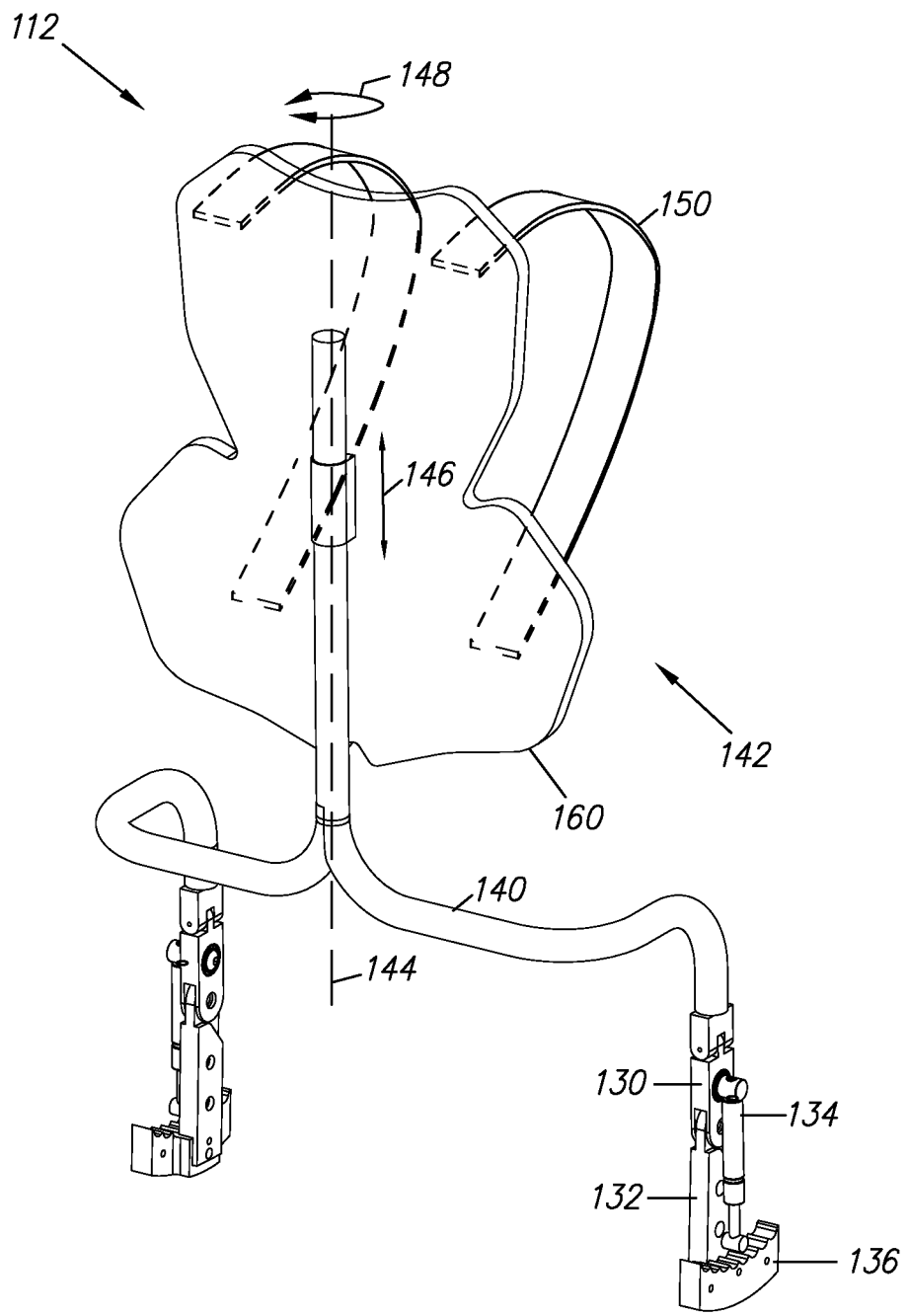
FIG. 7 depicts a human interface embodiment of the supporting trunk.

In some embodiments, human interface 142 comprises a back panel 160 to interface the person's back, as depicted in FIG. 7. In some embodiments, back panel 160 is compliant and deforms as the person bends. In some embodiments, human interface 142 further comprises at least one shoulder strap 150 configured to couple to the person. Referring back to the embodiment of FIG. 1, a front panel 151 is provided and adapted to engage the front of a person's trunk 114, to provide additional support. Human interface 142 comprises any material or combination of materials capable of performing the indicated functions. Examples of materials of human interface 142 include, without limitation, fabric materials, plastic materials, belts, leather materials, carbon fiber materials, metallic materials, and combinations thereof.

In some embodiments, as shown in FIG. 7, human interface 142 is slide-able along axis 144 with respect to frame 140 (i.e. slide-able along a length of frame 140). This sliding movement, shown by arrow 146, facilitates the bending maneuver of the wearer.

In some embodiments, as shown in FIG. 7, human interface 142 is rotatable around axis 144 with respect to frame 140. Arrow 148 shows this rotational movement. This rotation allows the person to twist his/her upper body without moving the person's legs.

Figure 8:
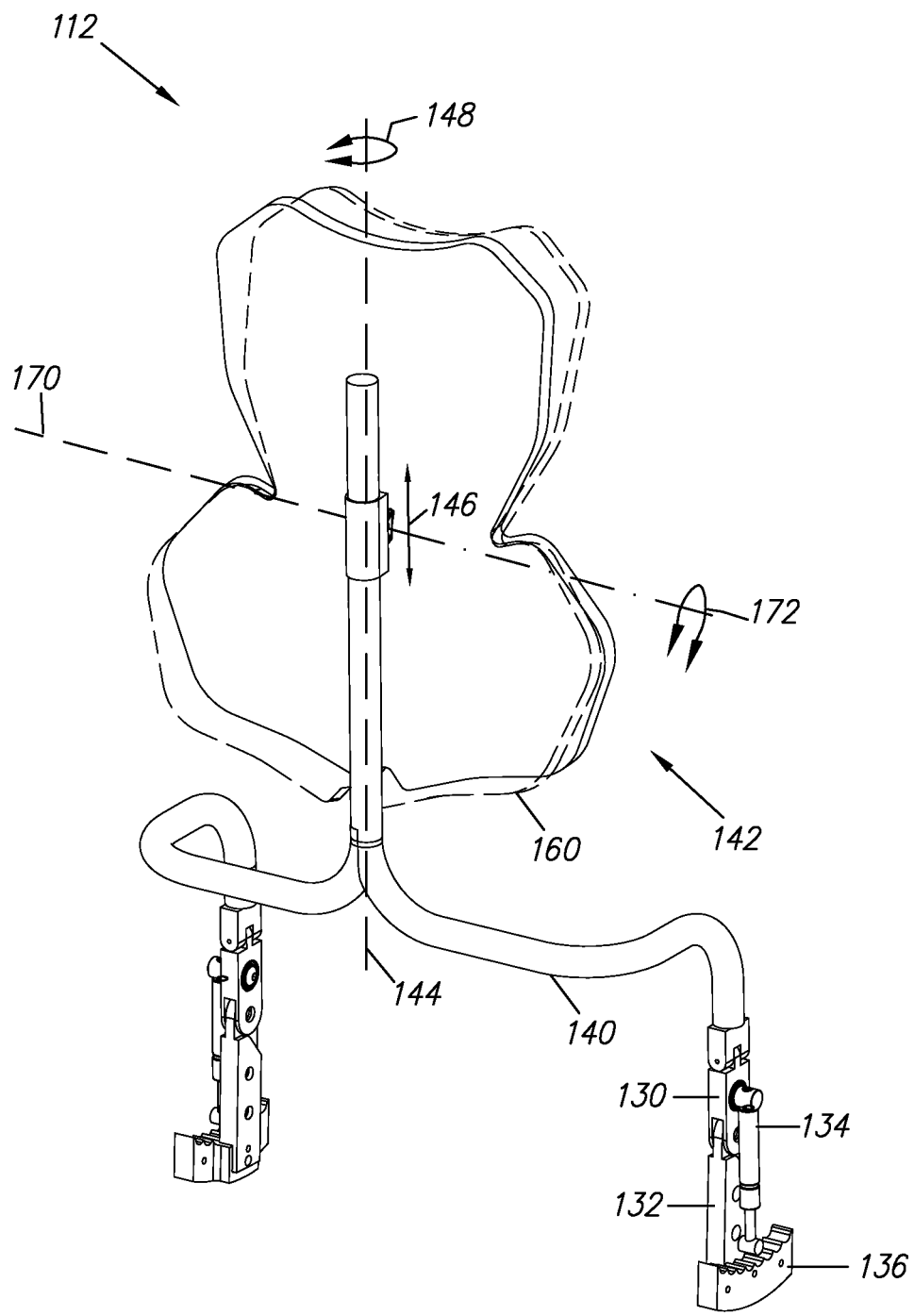
FIG. 8 depicts another human interface embodiment of the supporting trunk.

In some embodiments, as shown in FIG. 8, human interface 142 is rotatable around axis 170 with respect to frame 140. Arrow 172 shows this rotational movement. This rotation facilitates the bending maneuver of the person.

Figure 13:
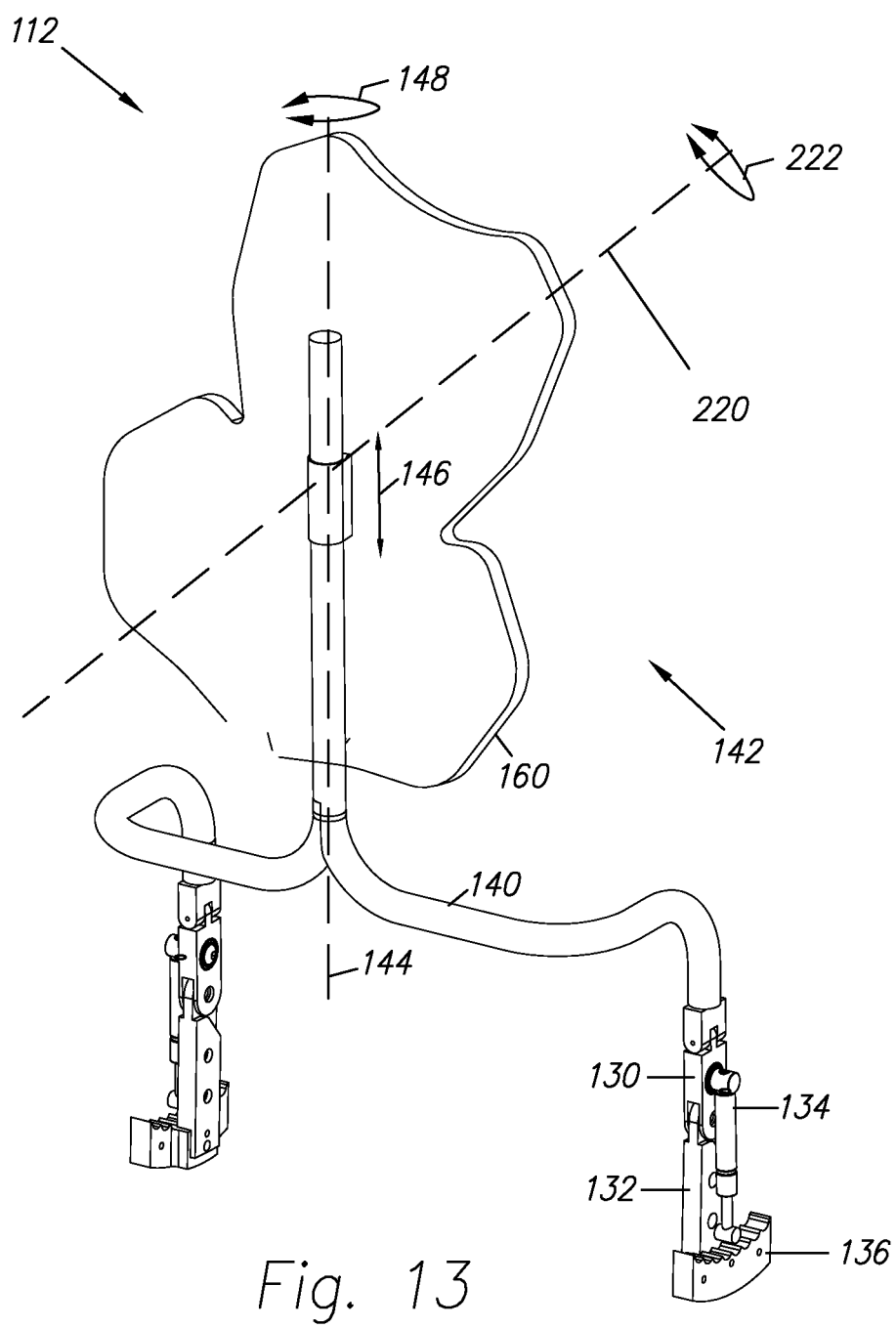
FIG. 13 depicts another human interface embodiment of the supporting trunk.

In some embodiments, as shown in FIG. 13, human interface 142 is rotatable around axis 220 with respect to frame 140. Arrow 222 shows this rotational movement. This rotation facilitates the rotational maneuver of the person.

In some embodiments, thigh links 104 and 106 each further comprise at least one thigh strap 180 and 182 configured to couple to wearer's thighs 108 and 110, as depicted in Figures. Thigh straps 180 and 182 comprise any material or combination of materials capable of performing the indicated functions. Examples of materials of thigh straps 180 and 182 include, without limitation, fabric materials, plastic materials, belts, leather materials, carbon fiber materials, metallic materials, and combinations thereof.

Figure 9:
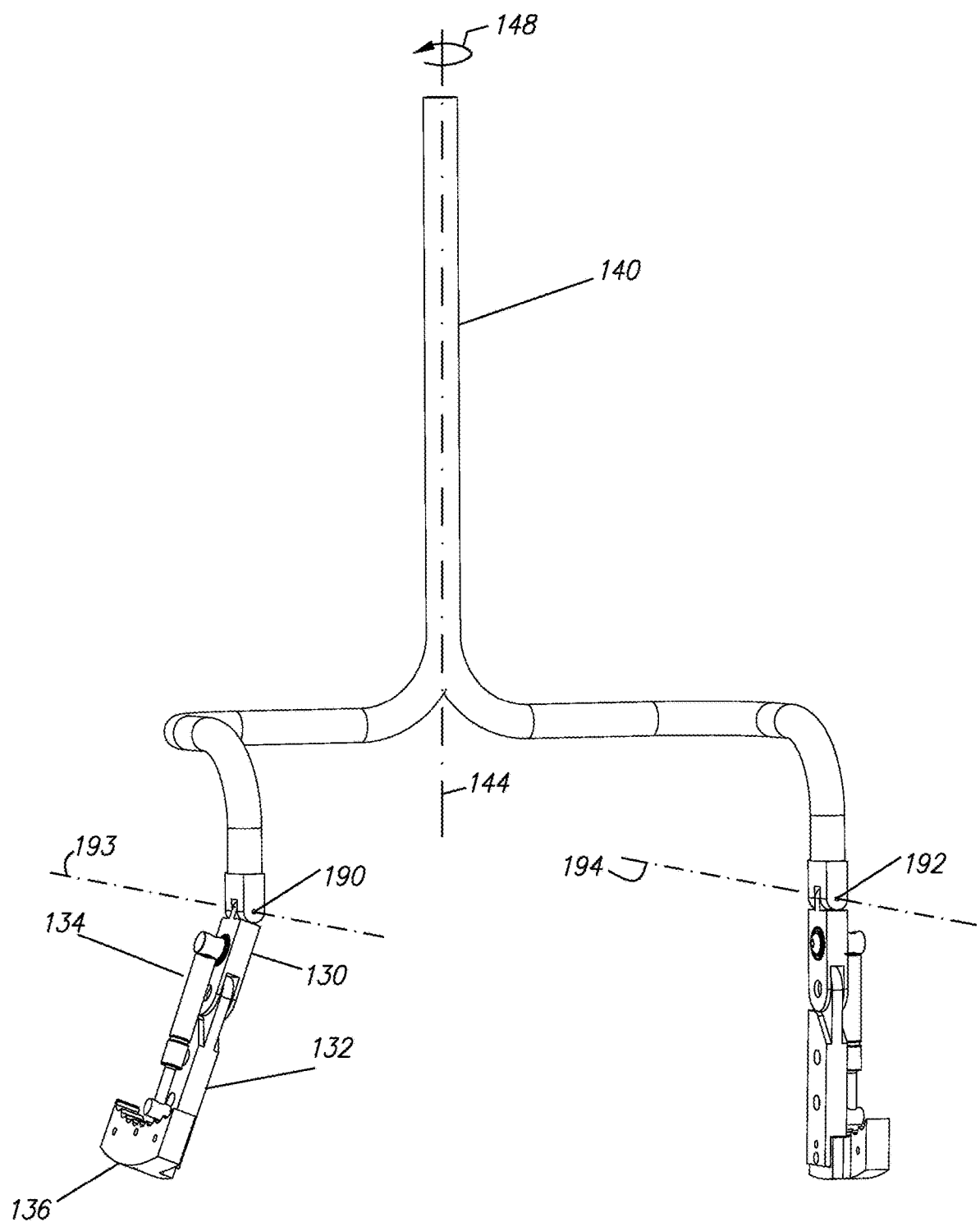
FIG. 9 depicts a portion of the exoskeleton embodiment with abduction and adduction capability.

In some embodiments, as shown in FIG. 9, frame 140 further comprises two rotary abduction-adduction joints 190 and 192 allowing for abduction and adduction of respective thigh links 104 and 106 relative to supporting trunk 112. As shown in FIG. 9, axes 193 and 194 represent the axes of abduction and adduction joints. FIG. 9 shows a portion of supporting trunk 112 where thigh link 104 has abducted.

Although described with reference to preferred embodiments, it should be readily understood that various changes, modifications, or both could be made to the description without departing from the spirit thereof. For instance, the various human interfaces, thigh straps, and torque generators can be combined in various ways to form different overall embodiments of the present disclosure. In general, the disclosure is only intended to be limited by the scope of the following claims.

An ordinary person skilled in the art would understand that there are several manufacturing methods for construction of upper bracket 130 and frame 140. One can fabricate upper bracket 130 separately and then couple it to frame 140 either by fasteners, through welding or other common engineering coupling methods. Although, FIGS. 4 and 5 show that upper bracket 130 is coupled to frame 140, one can manufacture frame 140 or supporting trunk 112 to include upper bracket 130 as one piece. Additionally although FIGS. 4 and 5 show that engagement bracket 136 is securely coupled onto lower bracket 132, one can manufacture these two parts as one piece. Although FIGS. 4 and 5 show that lower bracket 132 is securely coupled onto thigh link 104, one can manufacture these two parts as one piece.

Figure 14:
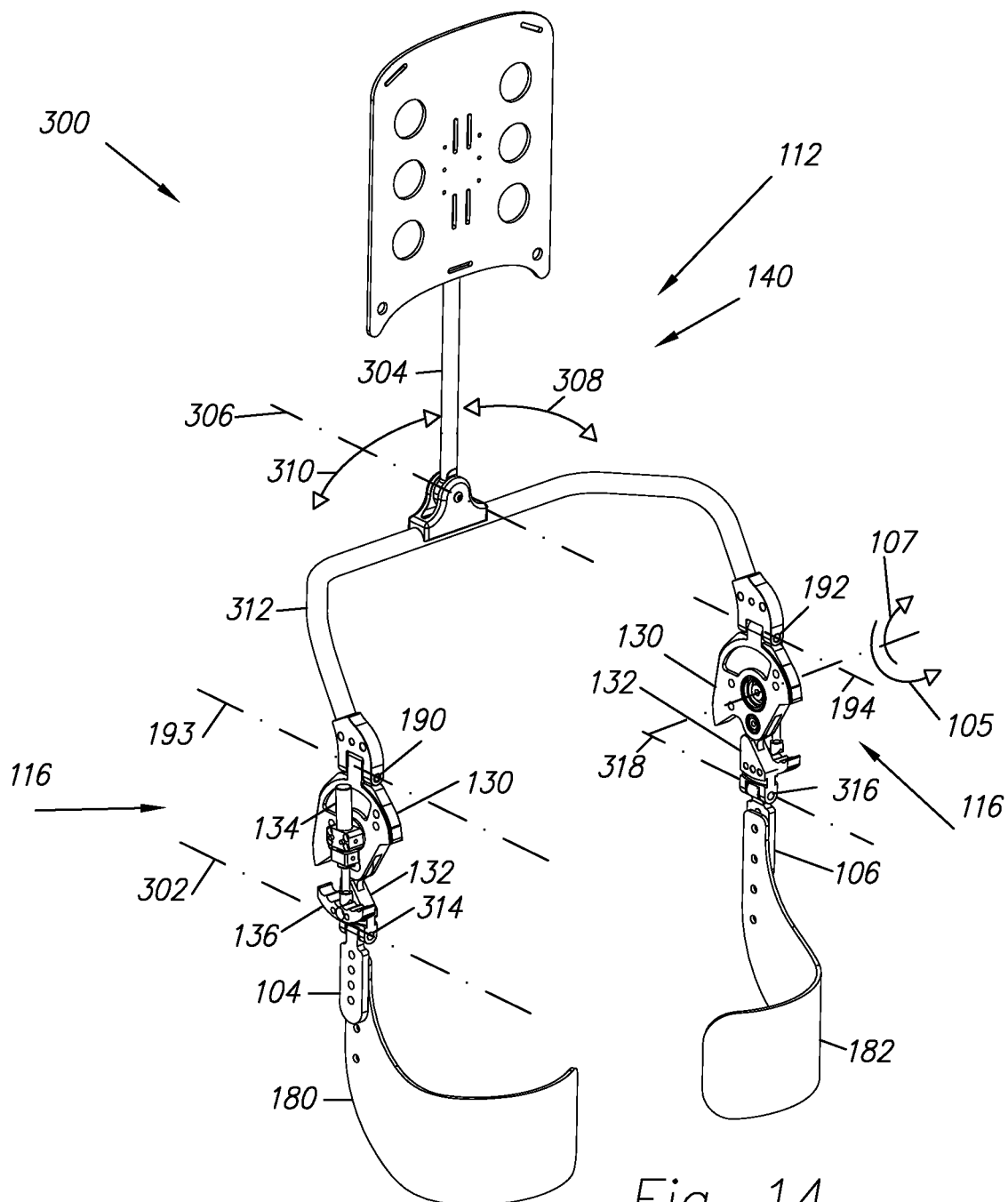
FIG. 14 depicts an embodiment of the trunk supporting exoskeleton.

FIG. 14 illustrates another embodiment of trunk supporting exoskeleton 300, which is configured to be worn by a person or wearer. The person is not shown in FIG. 14; however, exoskeleton 300 is worn like exoskeleton 100 as shown in FIGS. 1, 3 and 4. Trunk supporting exoskeleton 300 reduces the muscle forces in the wearer's back during forward lumbar flexion, in addition to other functions. In general, trunk supporting exoskeleton 300 comprises two thigh links 104 and 106, which are configured to be coupled to a wearer's thighs; and a supporting trunk 112, which is configured to be coupled to the person's trunk 114. Supporting trunk 112 is rotatably coupled to thigh links 104 and 106, allowing for the flexion and extension along arrows 105 and 107 of thigh links 104 and 106 with respect to supporting trunk 112. Additionally, trunk supporting exoskeleton 300 includes first and second opposing torque generators 116 and 118 capable of creating torques between supporting trunk 112 and respective first and second thigh links 104 and 106. It should be understood that the flexion and extension along arrows 105 and 107 of thigh links 104 and 106 with respect to supporting trunk 112 take place at the same location that human legs rotate relative to the human trunk. This colocation of axes allows little or no sliding motion between the trunk supporting exoskeleton components and the wearer. If the axes of rotation of thigh links 104 and 106 relative to supporting trunk 112 are not co-located with the human leg flexion and extension axes, then the supporting trunk 112 and thigh links 104 and 106 may slide relative to human trunk and human legs during flexion and extension.

As shown previously, supporting trunk 112 comprises a human interface 142, which is configured to be coupled to a person's trunk 114, and a frame 140, which is configured to be coupled to human interface 142. Frame 140 is rotatably coupled to thigh links 104 and 106 allowing for extension and flexion of thigh links 104 and 106 relative to frame 140. Frame 140 comprises any material or combination of materials capable of performing the indicated functions. In some embodiments, as shown in FIG. 14, frame 140 comprises of a waist frame 312 and a spine frame 304 rotatably coupled to each other. Axis 306 represents the rotation axis of spine frame 304 relative to waist frame 312. Arrows 308 and 310 show the directions of movements of spine frame 304 relative to waist frame 312. In some embodiments, waist frame 312 is substantially parallel with the person's hip line. In some embodiments, spine frame 304 is substantially parallel with the user's spine.

Figure 21:
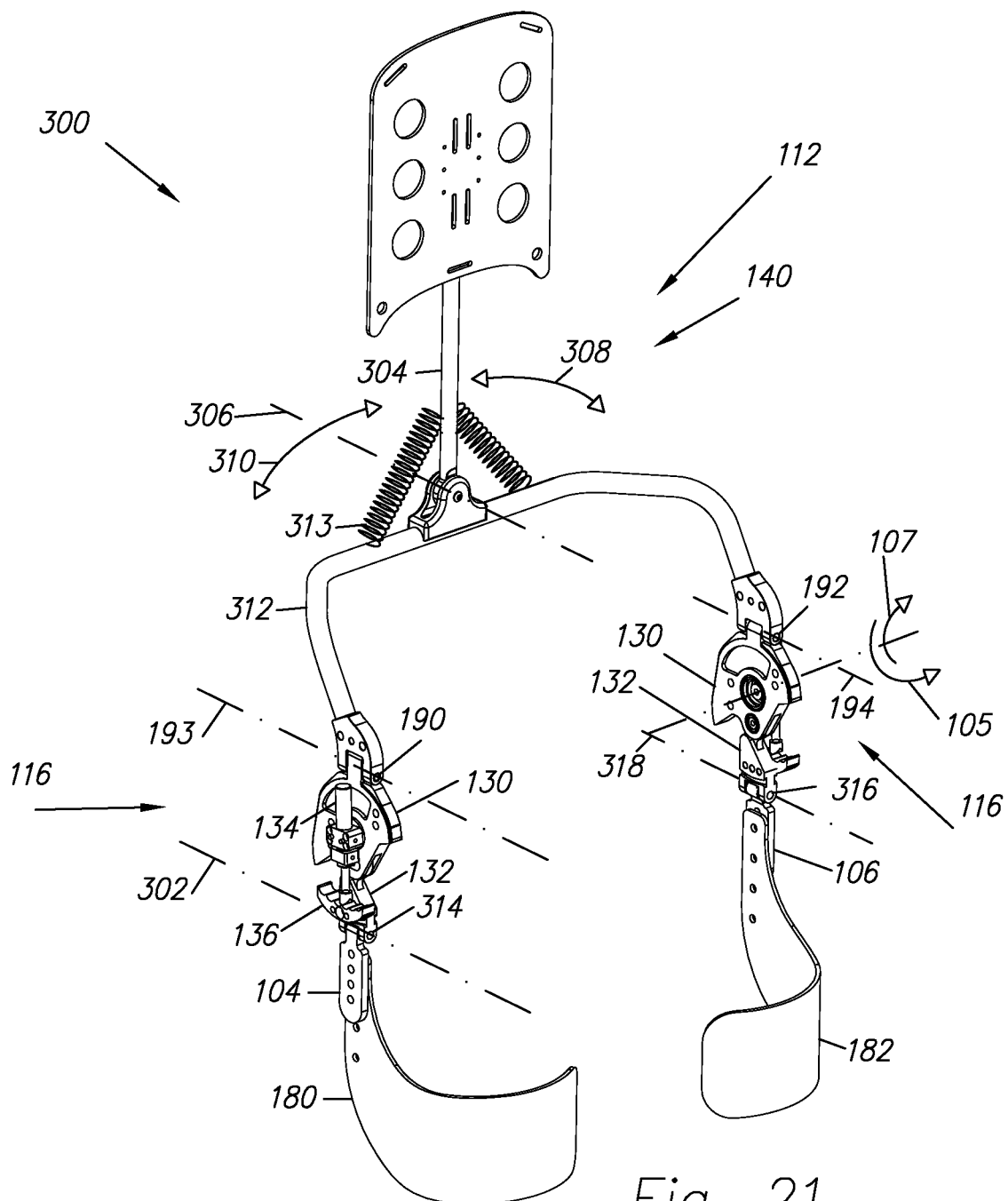
FIG. 21 depicts an embodiment of a trunk supporting exoskeleton.

In some embodiments, as shown in FIG. 21, frame 140 comprises at least one resilient element 313 that resists the rotation of spine frame 304 relative to waist frame 312. The force or moment of resilient element 313 causes spine frame 304 and waist frame 312 to remain orthogonal to each other. Resilient element 313 comprises any device or combination of devices capable of performing the indicated functions. Examples of resilient element 313 include, without limitation, gas spring, air spring, leaf spring, torsional spring compression spring, linear spring, tensile spring, and combinations thereof.

In some embodiments, as shown in FIG. 14, frame 140 further comprises two rotary abduction-adduction joints 190 and 192 allowing for abduction and adduction of respective thigh links 104 and 106 relative to supporting trunk 112. As shown in FIG. 14, axes 193 and 194 represent the axes of abduction and adduction joints. In some embodiments, as shown in FIG. 14, thigh links 104 and 106 further comprise two other rotary joints 314 and 316 allowing for rotation of respective thigh links 104 and 106 relative to lower bracket 132. As shown in FIG. 14, axes 302 and 318 represent the axes of rotations of thigh links 104 and 106 relative to lower bracket 132. Although FIG. 14 depicts that axes 302 and 318 are all parallel with axes 193 and 194, an ordinary skilled in the art would understand that in general the orientations of axes 302 and 318 relative to axes 193 and 194 depend on the flexion and extension of thigh links 104 and 106.

Figure 15:
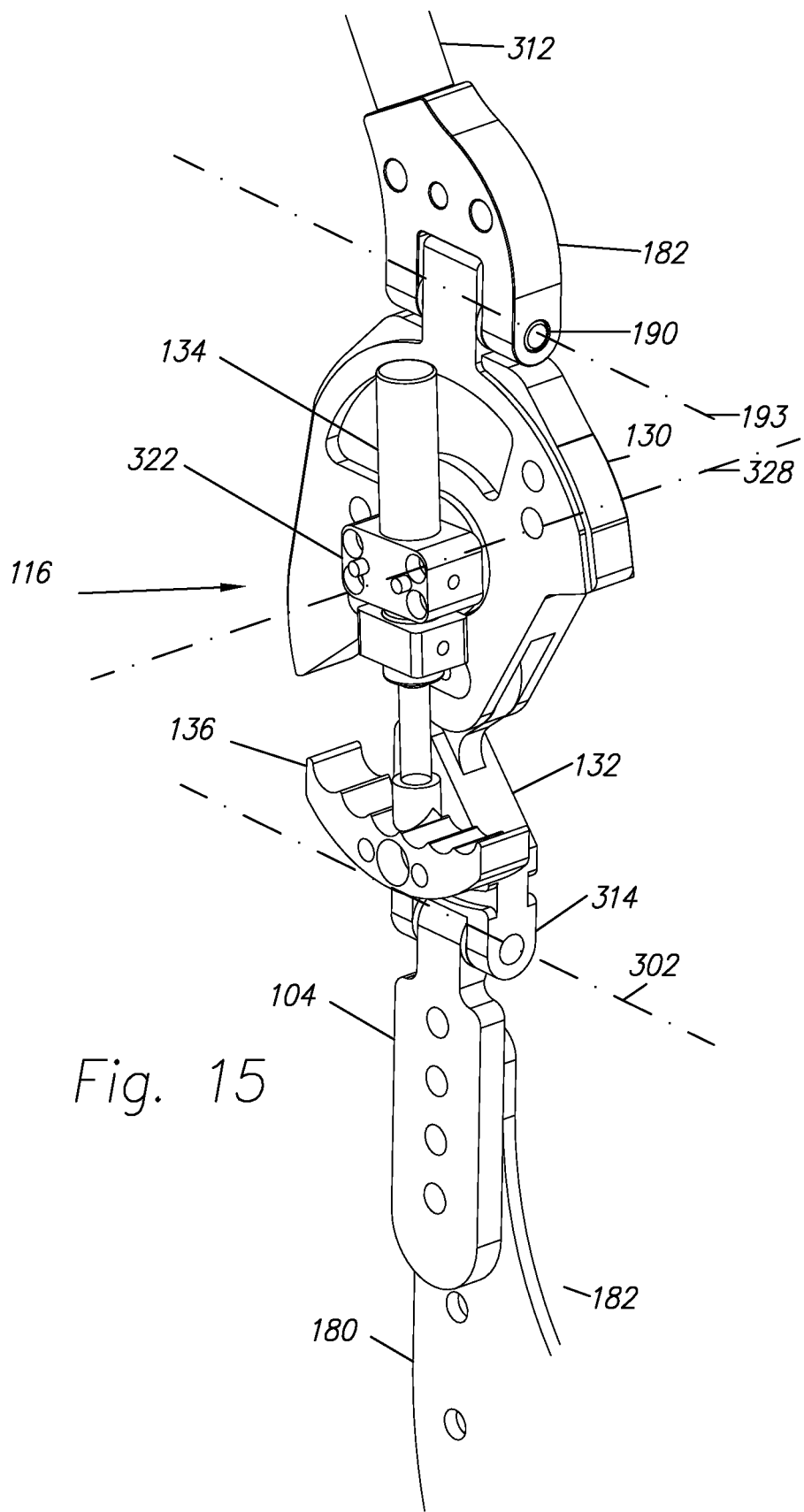
FIG. 15 depicts an embodiment of torque generator.

In some embodiments, resilient pendulum 134 is rotatably coupled to upper bracket 130 from its end as shown in FIGS. 4 and 5. In some other embodiments as shown in FIG. 15 and FIGS. 16A-16B resilient pendulum 134 is rotatably coupled to upper bracket 130 such that the location of the rotating point 320 of resilient pendulum 134 relative to upper bracket 130 is adjustable. FIGS. 16A-16B show an embodiment where a holding block 322 is rotatably coupled to upper bracket 130. Axis 328 (shown in FIG. 15) shows the axis of rotation of holding block 322 relative to upper bracket 130. Rotating point 320 represents the rotating point of holding block 322 relative to upper bracket 130. Resilient pendulum 134 is secured to holding block 322. In this embodiment, the location of rotating point 320 of resilient pendulum 134 can be adjusted relative to holding block 322. FIG. 16 shows two configurations of torque generator 116 where the position of resilient pendulum 134 has been adjusted. The figure on the right shows the case where resilient pendulum 134 is lowered as much as a distance D represented by 326. This adjustment allows for exoskeleton sensitivity as to what torso angle resilient pendulum 134 would get engaged with engagement bracket 136.

Figure 17B:
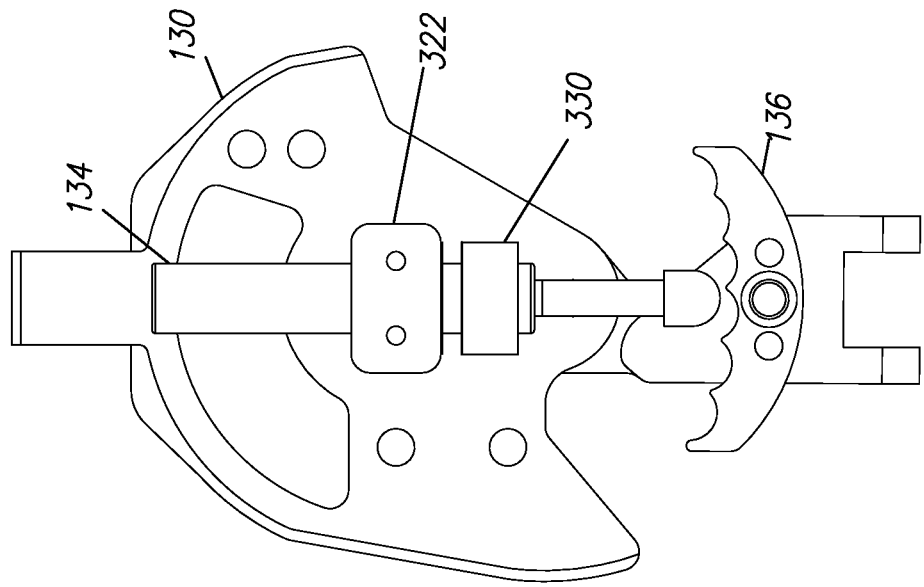
FIGS. 17A-17B depict an embodiment of torque generator.
Figure 17A:
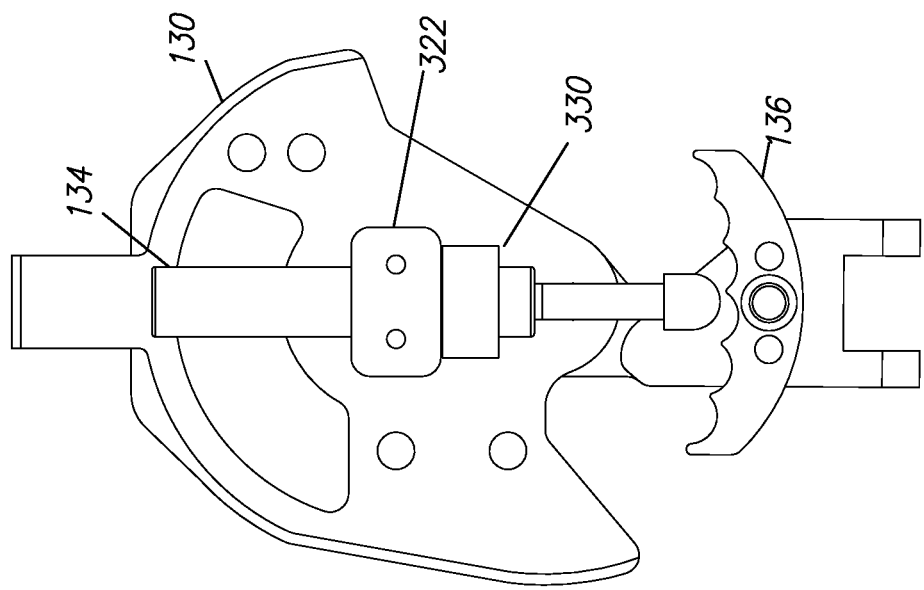

Resilient pendulum 134 comprises any device or combination of devices capable of performing the indicated functions. Examples of resilient pendulum 134 include, without limitation, gas spring, air spring, leaf spring, torsional spring, compression spring, linear spring, tensile spring, and combinations thereof. In some embodiments as shown in FIGS. 17A-17B, a mass 330 is coupled to resilient pendulum 134. The location of mass 330 can be adjusted relative to resilient pendulum 134 to allow for desired natural frequency of resilient pendulum 134.

In some embodiments, torque generator 116 further comprises a locking system 400 to prevent the rotational motion of resilient pendulum 134 relative to upper bracket 130. In operation when the rotational motion of resilient pendulum 134 relative to upper bracket 130 is prevented, then resilient pendulum 134 moves in unison with upper racket 130 and resilient pendulum 134 will not be in contact with engagement bracket 136. This means no resisting torque is produced between upper bracket 130 and lower bracket 132. When the rotational motion of resilient pendulum 134 relative to upper bracket 130 is not prevented, then resilient pendulum 134 may contact engagement bracket 136 when the person bends and a torque is produced between upper bracket 130 and lower bracket 132.

Figure 18:
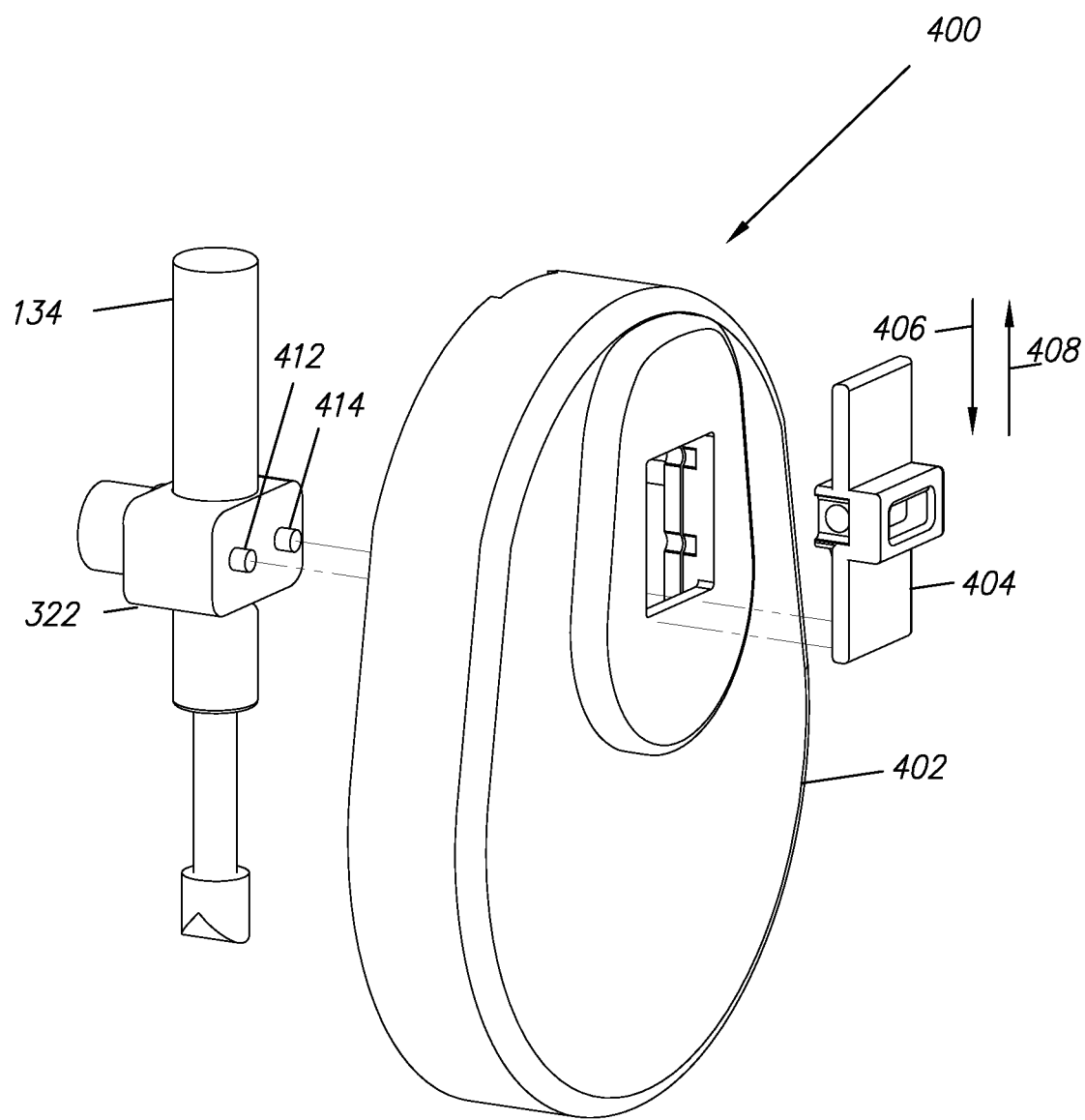
FIG. 18 depicts an embodiment of torque generator with a locking system.
Figure 19:
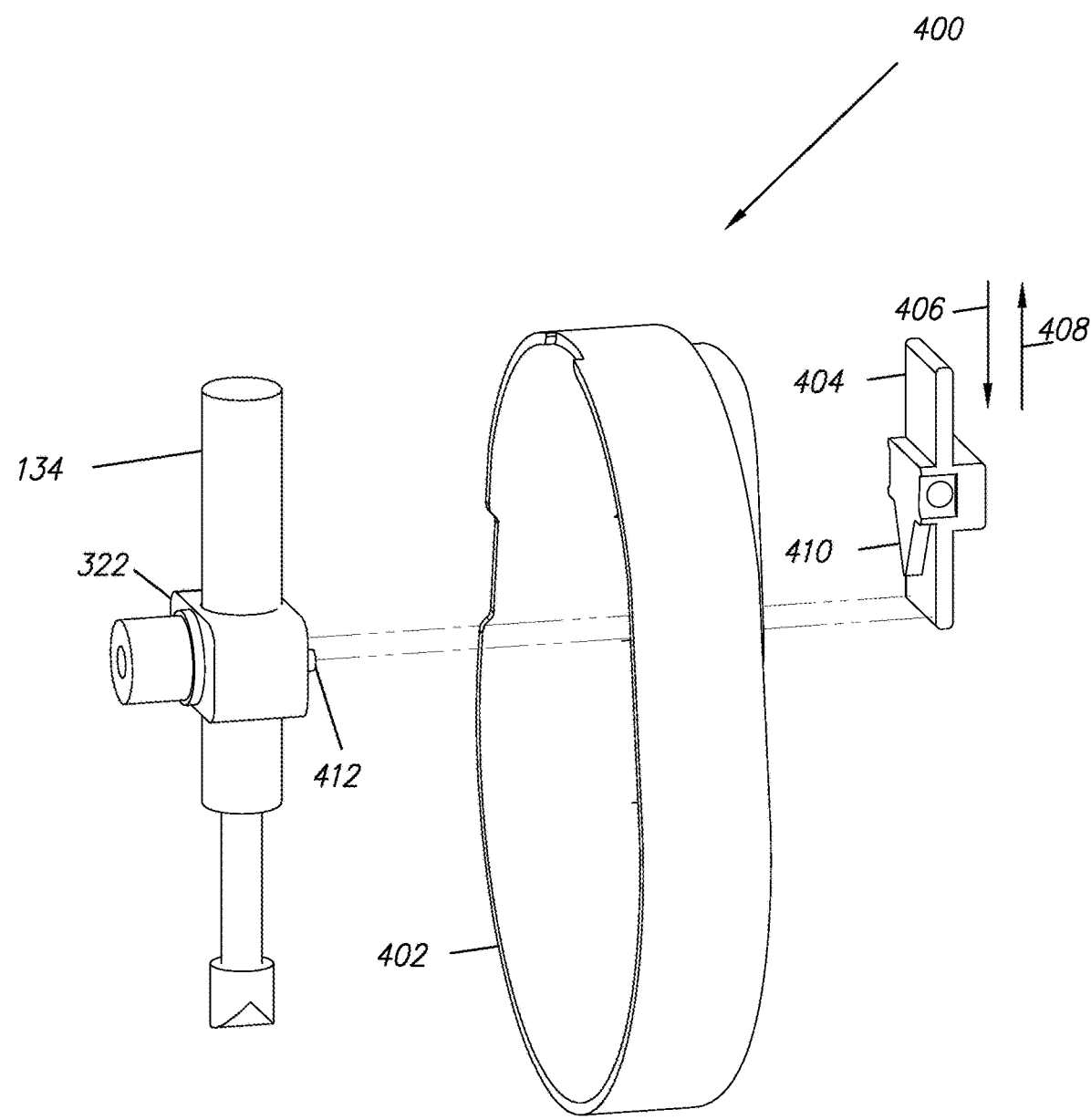
FIG. 19 depicts an embodiment of torque generator with a locking system.
Figure 20:
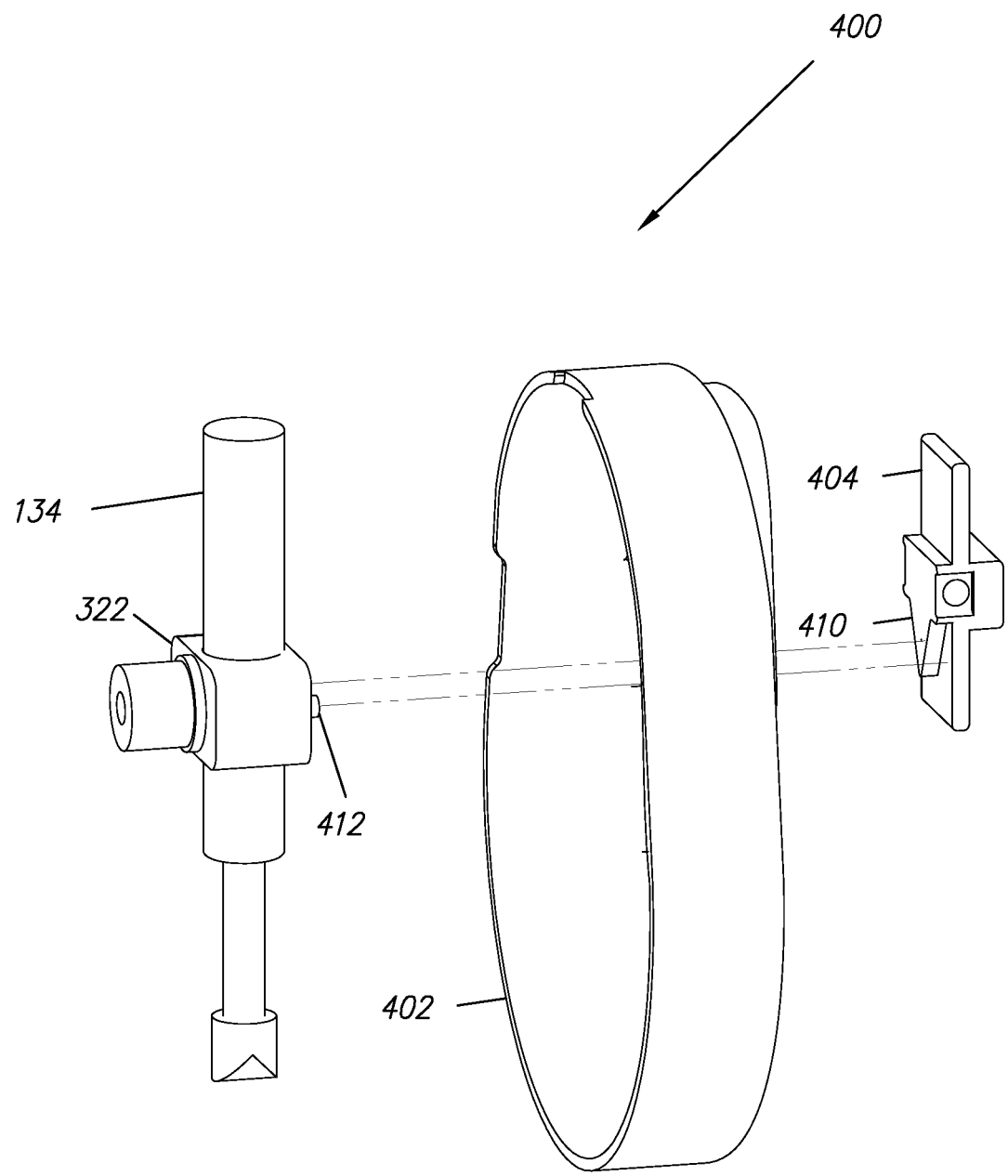
FIG. 20 depicts an embodiment of torque generator with a locking system.

FIGS. 18 and 19 show exploded views of an embodiment of locking system 400 from two different views. Locking system 400, among other components, comprises a cover bracket 402 coupled to upper bracket 130 and a moving bracket 404 capable of moving relative to cover bracket 402 along arrows 406 and 408. Moving bracket 404 further comprises at least one protrusion 410. This protrusion 410 can be made in a variety of shapes and geometry. In the embodiment shown in 19, protrusion 410 has a triangular shape. In the embodiment shown in FIGS. 18 and 19, resilient pendulum 134 or holding block 322 further includes two pendulum protrusions 412 and 414. In operation when moving bracket 404 is in its unlocked position (pushed up as shown in FIG. 19), protrusion 410 will not be in between pendulum protrusions 412 and 414 and will not prevent the motion of resilient pendulum 134 with respect to moving bracket 404. When moving bracket 404 is in its locked position (pushed down) as shown in FIG. 20, protrusion 410 moves in between pendulum protrusions 412 and 414 preventing the motion of resilient pendulum 134 with respect to moving bracket 404. In general, moving bracket 414 has at least two positions. When moving bracket 414 is in its first position, protrusion 410 will not prevent the motion of resilient pendulum 134 with respect to moving bracket 414 and when moving bracket 414 is in its second position, protrusion 410 will interfere the rotation of resilient pendulum 134 and will prevent the motion of resilient pendulum 134 with respect to moving bracket 414.

Figure 22:
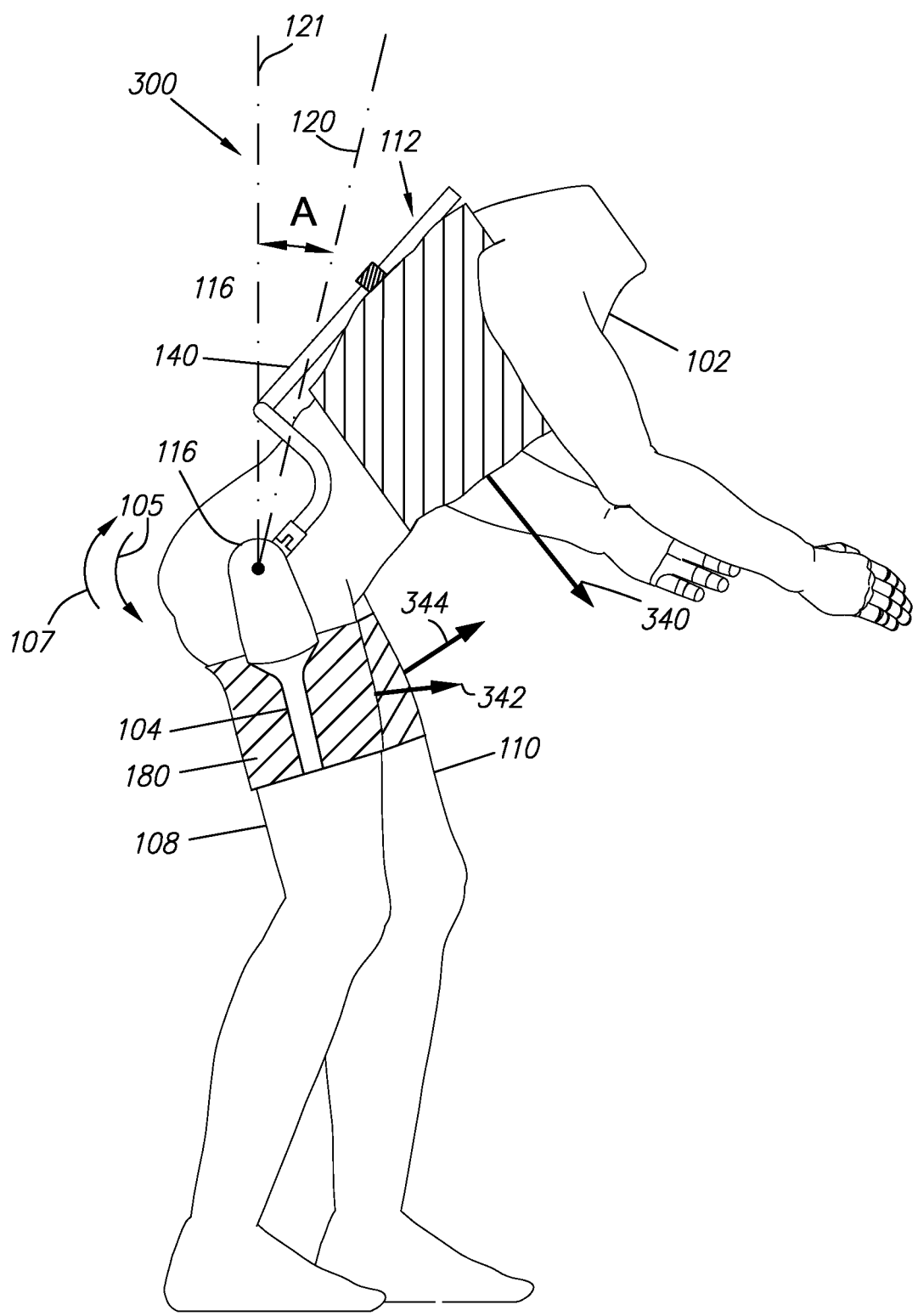
FIG. 22 depicts reaction forces from user onto trunk supporting exoskeleton.
Figure 23:
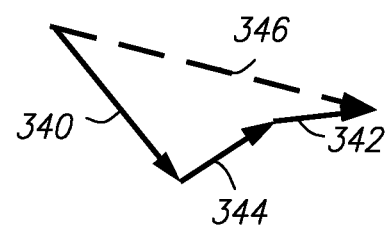
FIG. 23 depicts the addition of reaction forces.
Figure 24:
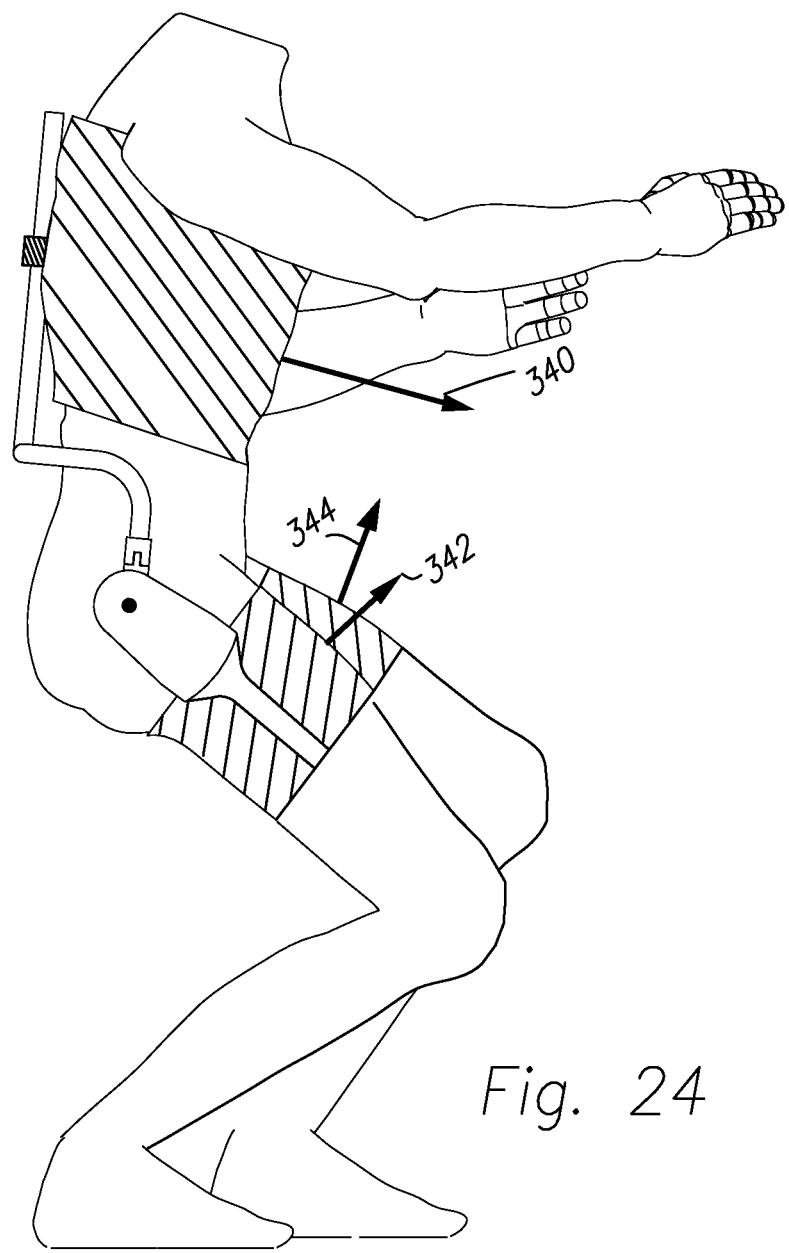
FIG. 24 depicts reaction forces from user onto trunk supporting exoskeleton.
Figure 25:
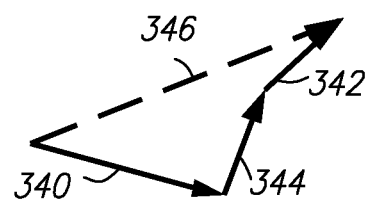
FIG. 25 depicts the addition of reaction forces.

As shown in FIG. 2, this device causes supporting trunk 112 to impose a force 122 onto a person's trunk 114, and thigh links 104 and 106 to impose forces 124 and 126 onto the wearer's respective thighs 108 and 110. As shown in FIG. 22 the reaction forces from user onto trunk supporting exoskeleton 300 are presented by 340, 342, and 344. In the quasi-static case, reaction forces 340, 342, and 344 are equal but in opposite directions to forces 122, 124, and 126. The addition of reaction forces 340, 342, and 344 results in a resultant force 346 on trunk supporting exoskeleton 300. Resultant force 346 changes its direction as a function of the person's posture. FIG. 23 shows resultant force 346 which is from left to right and slightly downwardly since the person has not squatted substantially. FIG. 24 shows another user's posture where the user has squatted deeper. As shown in FIG. 25, the resultant force 346 is from left to right and slightly upwardly. This indicates that trunk supporting exoskeleton 300 seeks to move toward the person (generally from the left to the right and slightly upwardly as shown in FIG. 25) and contact the person from back for equilibrium. It is best to ensure that the trunk supporting exoskeleton 300 contacts the person from the back in an ergonomic way. It is preferable that the force imposed on the user from trunk supporting exoskeleton 300 is imposed by soft components (made of fabric) rather than the hard components such as waist frame 312 and spine frame 304. It is therefore necessary that these soft components are secured to both the trunk supporting exoskeleton 300 and the user so the trunk supporting exoskeleton 300 does not move upwardly on the user. Additionally, it is preferable that the force from trunk supporting exoskeleton 300 is imposed on the proper location on the person and is distributed evenly on a large area on the person. To ensure the above condition, we suggest an antimoving support 350, which is configured to couple trunk supporting exoskeleton 300. Antimoving support 350 impedes the trunk supporting exoskeleton 300 from moving upwardly toward the person's shoulder when person 102 is squatting.

Figure 26:
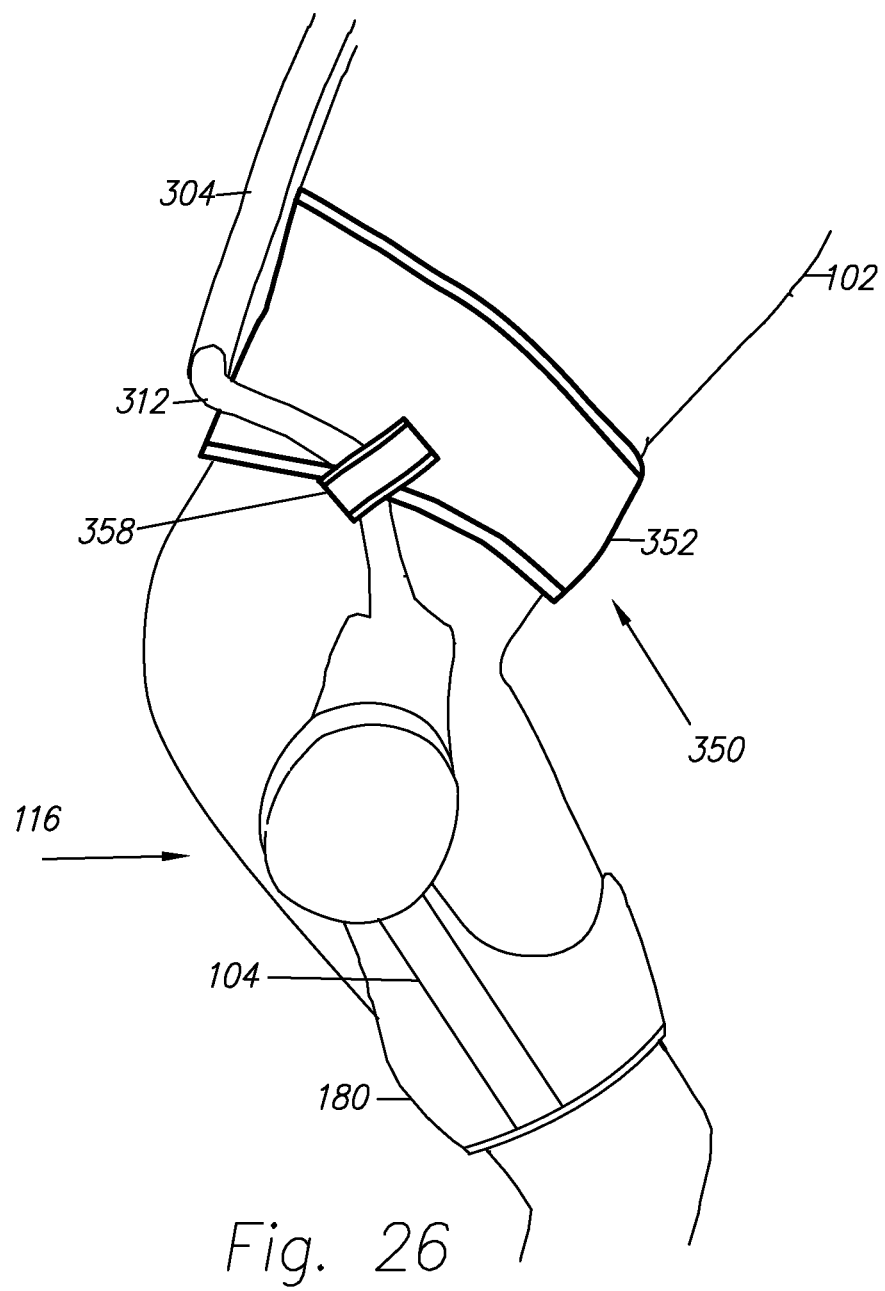
FIG. 26 depicts an embodiment of antimovement support.
Figure 27:
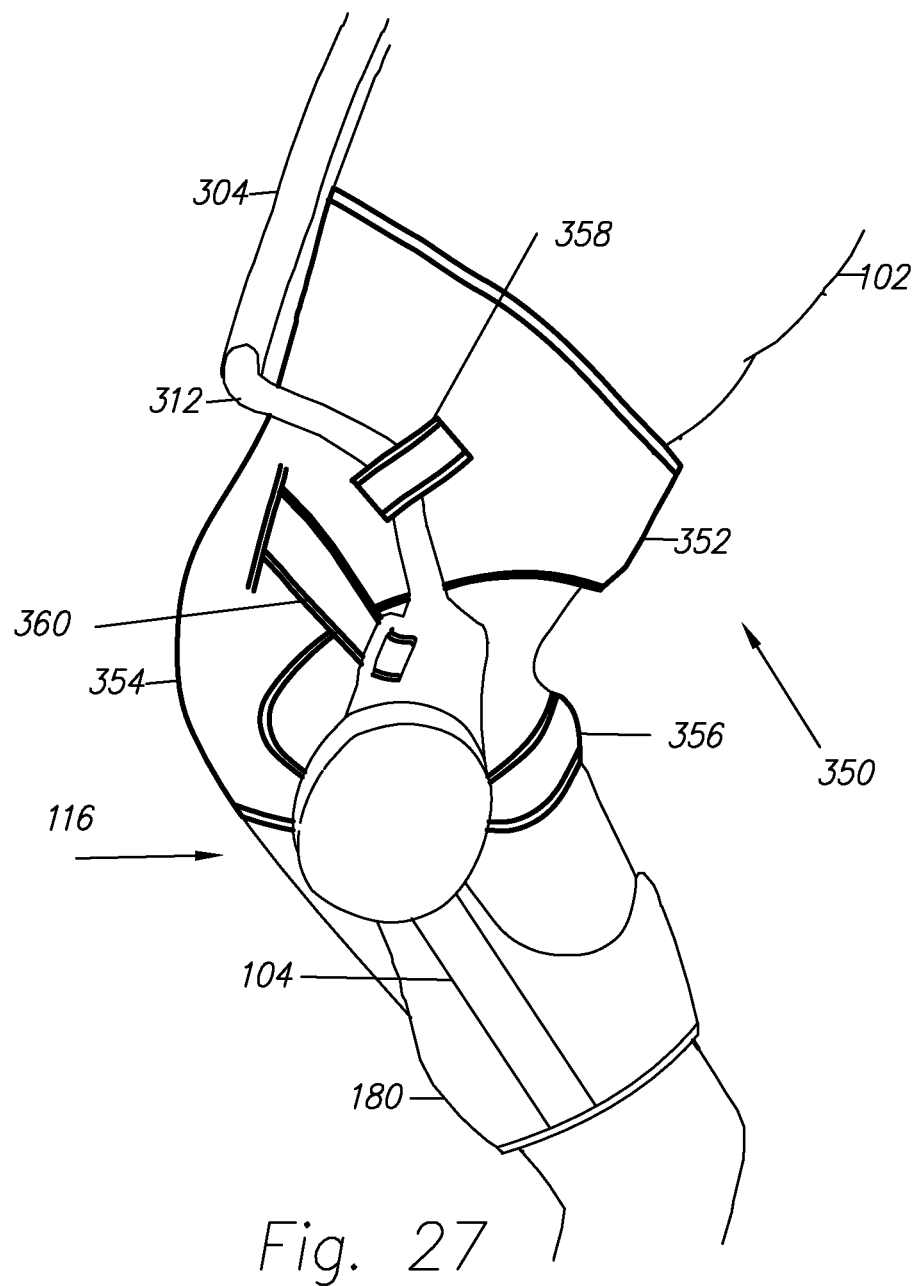
FIG. 27 depicts an embodiment of antimovement support.

In some embodiments as shown in FIG. 26, antimoving support 350 is a belt 352, which is configured to contact to person's hip area and to couple supporting trunk 112 at locations close to the rotation points of thigh links 104 and 106 relative to supporting trunk 112. As shown in FIG. 26, antimoving support 350 is coupled to waist frame 312 through a connecting loop 358. The length of belt 352 should be smaller than the length of frame 140 ensure that frame 140 will not come in contact with the wearer and the force imposed by the device on the user from the back is actually imposed by belt 352 and not by frame 140. In some embodiments as shown in FIG. 27, antimoving support 350 comprises a seat support 354, which is configured to contact the person's hip and buttock areas and to couple supporting trunk 112. As shown in FIG. 26, antimoving support 350 is coupled to waist frame 312 through a connecting loop 358 and connecting belt 360. In some embodiments, antimoving support 350 further comprises at least a thigh loop 356 configured to loop around the person's thigh. As shown in FIG. 27, thigh loop 356 is coupled to seat support 354. In some embodiments, antimoving support 350 comprises at least a thigh loop 356 which is coupled to a frame 140 and configured to loop around the person's thighs.

Figure 28:
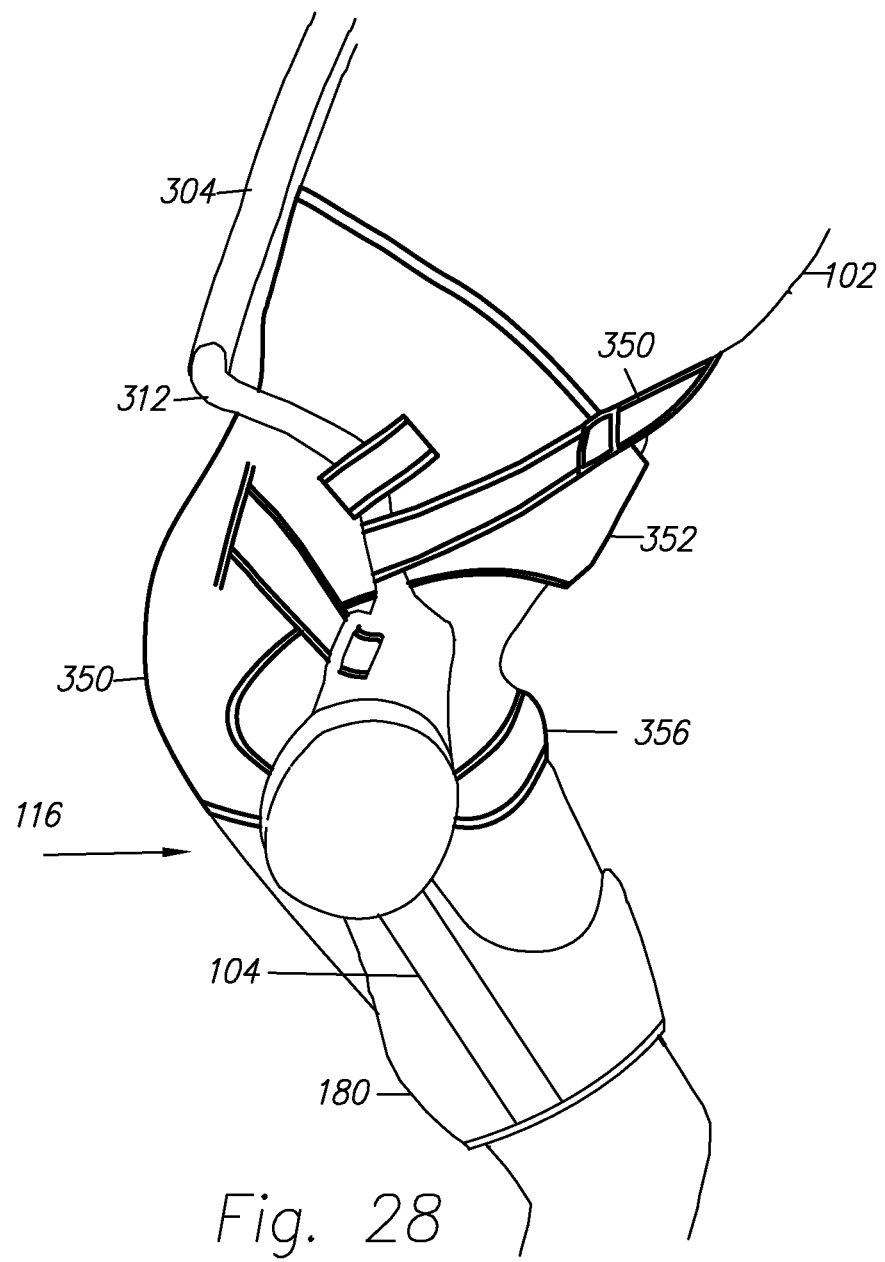
FIG. 28 depicts an embodiment of a trunk supporting exoskeleton.

In some embodiments, human interface 142 comprises a back panel 160 to interface the person's back, as depicted in FIG. 7. In some embodiments, human interface 142 further comprises at least one shoulder strap 150 configured to couple to the person. In some embodiments as shown in FIG. 28, human interface 142 comprises a back panel configured to interface with a wearer's back and a pair of shoulder straps configured to be coupled to back panel 160 and frame 140.

This disclosure has been presented for the purposes of illustration and description. It is not intended to be exhaustive or to limit the disclosure to the precise form described, and many modifications and variations are possible in light of the teaching above. The embodiments were chosen and described in order to best explain the principles of the disclosure and its practical applications. This description will enable others skilled in the art to best utilize and practice the disclosure in various embodiments and with various modifications as are suited to a particular use. The scope of the disclosure is defined by the following claims.

The invention claimed is:

1. A trunk supporting exoskeleton configured to be worn by a person to reduce muscle forces in a back of the person during forward lumbar flexion, the trunk supporting exoskeleton comprising:
   a supporting trunk, configured to be coupled to a trunk of the person;
   two thigh links, configured to couple to thighs of the person and rotatably coupled to the supporting trunk in a manner that allows for flexion and extension of the two thigh links relative to the supporting trunk;
   two active torque generators, capable of imposing a resisting torque between the supporting trunk and the two thigh links;
   a sensor generating an input signal representing the angle of the supporting trunk from a vertical line; and
   a signal processor,
   wherein the signal processor is configured to produce a control signal for the two active torque generators based on the input signal from the sensor,
   wherein when the person bends forward in a sagittal plane such that the supporting trunk extends beyond a predetermined angle from the vertical line, the signal processor produces the control signal for the two active torque generators and the two active torque generators impose the resisting torque between the supporting trunk and the two thigh links, causing the supporting trunk to impose a force against the trunk of the person thereby reducing the bending moment of the back of the person during a forward move,
   wherein the control signal increases the resisting torque imposed by the two active torque generators as the angle of the supporting trunk from the vertical lines increases, and
   wherein when the supporting trunk does not extend beyond the predetermined angle from the vertical line, the two active torque generators do not impose a resisting torque between the supporting trunk and the two thigh links over an entire range of motion of the two thigh links.

2. The trunk supporting exoskeleton of claim 1, wherein the two active torque generators are selected from the group consisting of alternating current (AC) motors, brush-type direct current (DC) motors, brushless DC motors, electric motors with transmission, electronically commutated motors (ECMs), stepping motors, and combinations thereof.

3. The trunk supporting exoskeleton of claim 1, further comprising a controller configured to automatically adjust an amount of the resisting torque imposed by the two active torque generators.

4. The trunk supporting exoskeleton of claim 1, further comprising a controller configured to automatically adjust an amount of the resisting torque imposed by the two active torque generators as a function of an angle between the trunk of the person and the vertical line.

5. The trunk supporting exoskeleton of claim 1, further comprising a controller configured to automatically adjust an amount of the resisting torque imposed by the two active torque generators as a function of the angle between the supporting trunk and the vertical line.

6. The trunk supporting exoskeleton of claim 1, wherein the sensor is selected from the group consisting of a velocity sensor, an accelerometer, a force sensor, a pressure sensor, an angle sensor, gyro, and a combination thereof.

7. The trunk supporting exoskeleton of claim 1, wherein the supporting trunk comprises:
a human interface, configured to be coupled to the trunk of the person, and
a frame, configured to be coupled to the human interface, wherein the frame is rotatably coupled to the two thigh links and allows for extension and flexion of the two thigh links relative to the supporting trunk.

8. The trunk supporting exoskeleton of claim 7, wherein the frame further comprises first and second rotary abduction-adduction joints, enabling abduction and adduction of the two thigh links relative to the supporting trunk.

9. A trunk supporting exoskeleton configured to be worn by a person to reduce muscle forces in a back of the person during forward lumbar flexion, the trunk supporting exoskeleton comprising:
a supporting trunk, configured to couple to a trunk of the person;
first and second thigh links, configured to couple to thighs of the person, wherein each of the first and second thigh links is rotatably coupled to the supporting trunk in a manner that allows for flexion and extension of respective ones of the first and second thigh links relative to the supporting trunk along a hip flexion axis of the person and on a location where legs of the person rotate relative to a trunk of the person;
an anti-moving support, coupled to the trunk supporting exoskeleton and configured to contact the person's hip and buttock areas in a manner such that the anti-moving support impedes the trunk supporting exoskeleton from moving relative to the person when the person is bending;
two torque generators, wherein each of the two torque generators is configured to impose resisting torque between the respective ones of the first and second thigh links and the supporting trunk;
a sensor configured to generate an input signal representing an angle of the supporting trunk from a vertical line; and
a signal processor,
wherein the signal processor is configured to produce a control signal for the two torque generators based on the input signal from the sensor, and
wherein when the person bends forward in a sagittal plane such that the angle of the supporting trunk from the vertical line is greater than a predetermined angle, at least one of the two torque generators imposes the resisting torque between the supporting trunk and at least one of the first and second thigh links thereby reducing the bending moment on the back of the person during the forward bend,
wherein when the angle of the supporting trunk from the vertical line is not greater than the predetermined angle, the two torque generators do not impose the resisting torque between the supporting trunk and at least one of the first and second thigh links over an entire range of motion of the first and second thigh links.

10. The trunk supporting exoskeleton of claim 9, wherein the anti-moving support comprises a belt, configured to couple a hip area of the person and to couple the supporting trunk, and wherein forward flexion of the supporting trunk from a vertical line does not cause substantial motion for the trunk supporting exoskeleton relative to the person.

11. The trunk supporting exoskeleton of claim 10, wherein the belt is coupled to the supporting trunk.

12. The trunk supporting exoskeleton of claim 10, wherein the belt is coupled to the supporting trunk at the person's hip or buttocks area.

13. The trunk supporting exoskeleton of claim 10, wherein the supporting trunk comprises: a human interface, configured to be coupled to the trunk of the person, and
a frame, configured to be coupled to the human interface; wherein said belt is coupled to the frame.

14. The trunk supporting exoskeleton of claim 9, wherein the anti-moving support comprises a seat support, configured to contact a buttock area of the person and to couple the supporting trunk, and wherein forward flexion of the supporting trunk from a vertical line does not cause substantial motion for the trunk supporting exoskeleton relative to the person.

15. The trunk supporting exoskeleton of claim 14, wherein the anti-moving support further comprises at least a thigh loop, configured to loop around at least one of the thighs of the person.

16. The trunk supporting exoskeleton of claim 15, wherein the thigh loop is coupled to the seat support.

17. The trunk supporting exoskeleton of claim 15, wherein the thigh loop is coupled to at least one of the first and second thigh links.

18. The trunk supporting exoskeleton of claim 14, wherein the seat support is coupled to the supporting trunk.

19. The trunk supporting exoskeleton of claim 14, wherein the seat support is coupled to the supporting trunk at the person's hip or buttocks area.

20. The trunk supporting exoskeleton of claim 9, wherein the anti-moving support further comprises at least a thigh loop, configured to loop around at least one of the thighs of the person, and wherein forward flexion of the supporting trunk from a vertical line does not cause substantial motion for the trunk supporting exoskeleton relative to the person.

21. The trunk supporting exoskeleton of claim 20, wherein the thigh loop is coupled to the supporting trunk.

22. The trunk supporting exoskeleton of claim 20, wherein the thigh loop is coupled to the supporting trunk at the person's hip or buttocks area.

23. The trunk supporting exoskeleton of claim 20, wherein the supporting trunk comprises:
a human interface, configured to be coupled to the trunk of the person, and a frame, configured to be coupled to the human interface, wherein the frame is rotatably coupled to the thigh links and allows for extension and flexion of the thigh links relative to the supporting trunk;

wherein said thigh loop is coupled to the frame.

24. The trunk supporting exoskeleton of claim 20, wherein the thigh loop is coupled to at least one of the first and second thigh links.

25. The trunk supporting exoskeleton of claim 9, wherein the two torque generators are selected from the group consisting of alternating current (AC) motors, brush-type direct current (DC) motors, brushless DC motors, electric motors with transmission, electronically commutated motors (ECMs), stepping motors, and combinations thereof.

26. The trunk supporting exoskeleton of claim 9, wherein the sensor is selected from the group consisting of a velocity sensor, an accelerometer, a force sensor, a pressure sensor, an angle sensor, an electric motor movement sensor, an electric motor speed sensor, an electric motor force sensor, gyro, and a combination thereof.

27. The trunk supporting exoskeleton of claim 9, wherein the anti-moving support impedes the trunk supporting exoskeleton from moving upwardly toward a shoulder of the person when the person is bending.

28. The trunk supporting exoskeleton of claim 9, wherein the anti-moving support is coupled to the supporting trunk.

29. The trunk supporting exoskeleton of claim 9, wherein the anti-moving support is coupled to the supporting trunk at the person's hip or buttocks area.

30. The trunk supporting exoskeleton of claim 9, wherein the supporting trunk comprises:

a human interface, configured to be coupled to the trunk of the person, and a frame, configured to be coupled to the human interface, wherein the frame is rotatably coupled to the thigh links and allows for the extension and flexion of the thigh links relative to the supporting trunk;

wherein the anti-moving support is coupled to the frame.

31. The trunk supporting exoskeleton of claim 30, wherein the anti-moving support is coupled to the frame at the person's hip or buttocks area.

32. The trunk supporting exoskeleton of claim 9, wherein said anti-moving support comprises an element or combination of elements selected from a group consisting of belts, seat supports, and thigh loops.

\* \* \* \* \*

UNITED STATES PATENT AND TRADEMARK OFFICE
CERTIFICATE OF CORRECTION

PATENT NO. : 12,029,674 B2
APPLICATION NO. : 16/375231
DATED : July 9, 2024
INVENTOR(S) : Kazerooni et al.

It is certified that error appears in the above-identified patent and that said Letters Patent is hereby corrected as shown below:

In the Claims

In Column 14, Claim 1, Line 42, delete "the" replace with --an--.

In Column 14, Claim 1, Line 56, delete "the" replace with --a--.

In Column 14, Claim 1, Line 64, delete "a" replace with --the--.

Signed and Sealed this
Eighth Day of October, 2024

Katherine Kelly Vidal
*Director of the United States Patent and Trademark Office*